(12) United States Patent
Knowlton

(10) Patent No.: US 6,470,216 B1
(45) Date of Patent: *Oct. 22, 2002

(54) METHOD FOR SMOOTHING CONTOUR IRREGULARITIES OF SKIN SURFACE

(75) Inventor: Edward W. Knowlton, Danville, CA (US)

(73) Assignee: Thermage, Inc., Hayward, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/825,443

(22) Filed: Mar. 28, 1997

Related U.S. Application Data

(63) Continuation-in-part of application No. 08/583,815, filed on Jan. 5, 1996, now Pat. No. 6,241,753, which is a continuation-in-part of application No. 08/435,822, filed on May 5, 1995, now Pat. No. 5,755,753.
(60) Provisional application No. 60/023,377, filed on Aug. 6, 1996.

(51) Int. Cl.[7] .................................................. A61F 2/00
(52) U.S. Cl. ....................... 607/101; 607/102; 607/108; 607/112; 607/33
(58) Field of Search ............................... 606/27–34, 38, 606/44–52; 607/96–144

(56) References Cited

U.S. PATENT DOCUMENTS

| | | | |
|---|---|---|---|
| 3,831,604 A | * | 8/1974 | Neefe .......................... 604/20 |
| 4,074,718 A | | 2/1978 | Morrison |
| 4,140,130 A | | 2/1979 | Storm, III |
| 4,164,226 A | | 8/1979 | Tapper |

(List continued on next page.)

FOREIGN PATENT DOCUMENTS

| | | |
|---|---|---|
| DE | 1 949 534 | 4/1970 |
| DE | 31 21 683 | 12/1982 |
| EP | 0 519 415 | 12/1992 |
| FR | 2 609 245 | 7/1988 |
| NZ | 266678 | 12/1997 |
| WO | WO 92/19414 | 11/1992 |
| WO | 93/13816 | 7/1993 |
| WO | 94/26228 | 11/1994 |
| WO | 96/27240 | 9/1996 |
| WO | 96/27327 | 9/1996 |
| WO | 96/32051 | 10/1996 |
| WO | 96/34568 | 11/1996 |
| WO | 96/39914 | 12/1996 |
| WO | 97/18765 | 5/1997 |
| WO | 97/18768 | 5/1997 |
| WO | 68/03117 | 1/1998 |
| WO | 98/03220 | 1/1998 |

OTHER PUBLICATIONS

American Heritage Dictionary; Houghton Mifflin Co.; 1976, p. 309.*

(List continued on next page.)

*Primary Examiner*—Roy D. Gibson
(74) *Attorney, Agent, or Firm*—Paul Davis; Heller Ehrman White & McAuliffe

(57) ABSTRACT

A method to modify a skin surface or a soft tissue structure underlying the skin surface includes a template with a mechanical force application surface and a receiving opening to receive a body structure. The mechanical force application surface is configured to receive the body structure and apply pressure to the soft tissue structure. An energy delivery device is coupled to the template. The energy delivery device is configured to deliver sufficient energy to the template to form a template energy delivery surface.

18 Claims, 19 Drawing Sheets

U.S. PATENT DOCUMENTS

| | | |
|---|---|---|
| 4,290,435 A | 9/1981 | Waggott |
| 4,343,301 A | 8/1982 | Indech |
| 4,346,715 A | 8/1982 | Gammell |
| 4,375,220 A | 3/1983 | Matvias |
| 4,381,007 A * | 4/1983 | Doss .............................. 606/5 |
| 4,441,486 A | 4/1984 | Pounds |
| 4,545,368 A | 10/1985 | Rand et al. |
| 4,676,258 A | 6/1987 | Inokuchi et al. |
| 4,709,701 A | 12/1987 | Weber |
| RE32,849 E | 1/1989 | Wei et al. |
| 4,881,543 A | 11/1989 | Trembly et al. |
| 4,887,614 A | 12/1989 | Shirakami et al. |
| 4,889,122 A | 12/1989 | Watmough et al. |
| 4,944,302 A | 7/1990 | Hernandez et al. |
| 4,957,480 A | 9/1990 | Morenings |
| 4,962,761 A | 10/1990 | Golden |
| 4,976,709 A * | 12/1990 | Sand .............................. 606/5 |
| 5,003,991 A | 4/1991 | Takayama et al. |
| 5,133,351 A | 7/1992 | Masaki |
| 5,143,063 A | 9/1992 | Fellner |
| 5,186,181 A | 2/1993 | Franconi et al. |
| 5,190,517 A | 3/1993 | Zieve et al. |
| 5,230,334 A | 7/1993 | Klopotek |
| 5,249,575 A | 10/1993 | DiMino et al. |
| 5,282,797 A | 2/1994 | Chess |
| 5,304,169 A | 4/1994 | Sand |
| 5,315,994 A | 5/1994 | Guibert et al. |
| 5,334,193 A | 8/1994 | Nardella |
| 5,342,357 A | 8/1994 | Nardella |
| 5,348,554 A | 9/1994 | Imran et al. |
| 5,366,443 A | 11/1994 | Eggers et al. |
| 5,370,642 A | 12/1994 | Keller |
| 5,374,265 A | 12/1994 | Sand |
| 5,423,807 A | 6/1995 | Milder |
| 5,423,811 A | 6/1995 | Imran et al. |
| 5,437,662 A | 8/1995 | Nardella |
| 5,458,596 A | 10/1995 | Lax et al. |
| 5,462,521 A | 10/1995 | Brucker et al. |
| 5,464,436 A | 11/1995 | Smith |
| 5,496,312 A | 3/1996 | Klicek |
| 5,507,790 A | 4/1996 | Weiss |
| 5,569,242 A | 10/1996 | Lax et al. |
| 5,681,282 A | 10/1997 | Eggers et al. |
| 5,683,366 A | 11/1997 | Eggers et al. |
| 5,692,058 A | 11/1997 | Eggers et al. |
| 5,693,045 A | 12/1997 | Eggers |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |

OTHER PUBLICATIONS

Adrian, R. M. Treatment of Facial Telangiectasia Using the VersaPulse® Variable Pulse Width Frequency Doubled Neodymium:YAG Laser: A Case Report.

Chess, C.; Chess, Q. "Cool Laser Optics Treatment of Large Telangiestasia of the Lower Extremities." *J. Dermatol Surg Oncol.* 1993; 19:74–80.

Coulson, W. F. et al. "Nonablative Laser Treatment of Facial Rhytides: Animal Study." Abstract for BiOS '98 Symposium Conference: bo05—Cutaneous Applications of Lasers, Jan. 24–30, 1998, San Jose, CA.

Kincade, K. "Demand for Laser Resurfacing Soars: Quicker Healing, Less Risk of Scarring" *Dermatology Times.* 1995. 16(10).

Fitzpatrick, R. "Treatment of Wrinkles with the UltraPulse $CO_2$ Laser.".

Laser Aesthetics, Inc. "The Cool Touch Laser." Brochure.

Laser Aesthetics, Inc. "Cool Touch Model 130 Technical Specifications." Brochure.

National Health Communications, Inc. "New Laser Eliminates 'Lipstick Bleed'" Press Release Jul. 1993.

Allain, et al. "Isometric Tensions Developed During the Hydrothermal Swelling of Rat Skin", Connective Tissue Research, vol. 7, pp. 697–701, (1990).

Danielson, C. "Age–Related thermal stability and susceptibility to proteolysis of rat bone collagen", . . . chem, Great Britain, pp. 697–701, (1990).

Danielson, C. "Thermal stability of reconstituted collagin fibrils, shrinkage characteristics upon in vitro maturation", Mechanisms of Ageing and Development, vol. 15, pp. 269–278, (1981).

Kronick, et al. "The locations of collagens with different thermal stabilities in fibrils of bovine recticular dermis". Connective Tissue Research, vol. 18, pp. 123–134, (1988).

Mainster, M.A. "Ophthalmic applications of infrared lasers—thermal considerations", Visual Sci., pp. 414–420, Apr. 1979.

Pearce, et al. "Kinetic models of laser–tissue fusion processes", ISA, paper #93–044, pp. 355–360, (1993)..

* cited by examiner

METHOD FOR SMOOTHING CONTOUR IRREGULARITIES OF SKIN SURFACE

CROSS-REFERENCE TO RELATED APPLICATIONS

This application is a continuation-in-part of U.S. patent application Ser. No. 08/583,815, filed Jan. 5, 1996, now U.S. Pat. No. 6,241,753, which is a continuation-in-part U.S. patent application Ser. No. 08/435,822, filed May 5, 1995 now U.S. Pat. No. 5,755,753. This application also claims the benefit of Provisional Application Ser. No. 60/023,377, filed Aug. 6, 1996.

BACKGROUND OF THE INVENTION

1. Field of the Invention

This invention relates to a method and apparatus for modifying a soft tissue structure underlying a skin surface, and more particularly to a method and apparatus which applies a mechanical force and electromagnetic energy to the soft tissue structure.

2. Description of Related Art

The correction of a deformity or the esthetic enhancement of a soft tissue structure is determined by the balance of the skin envelope as the container and soft tissue volume as the contents of the container. An appropriate balance between these two components is essential in achieving a successful outcome. Most plastic surgery procedures are based upon the resection or addition of a soft tissue filler with a concomitant modification of the skin envelope. For example, a breast that has three dimensional symmetry with the opposite breast must take into account both the volume of the soft tissue and the surface area of the breast envelope that is required as a container of the tissue. Breast reconstruction after mastectomy typically involves the insertion of a soft tissue replacement for the removed breast tissue. Either an implant or a tissue flap from the patient is used as a soft tissue replacement. Expansion of the breast skin envelope is also required and is achieved with a medical device called a breast expander. While most reconstructive procedures usually involve the addition of a soft tissue filler with the expansion of the skin envelope, many esthetic procedures involve the reduction of the soft tissue contents with or without a reduction in the skin envelope. Reduction in the volume of the soft tissue contents without a concomitant reduction in the skin envelope may lead to a relative excess of the skin envelope. The relative excess will be visualized as loose skin or elastosis. An example of esthetic enhancement is a procedure called breast reduction. This is performed in women who require reduction in the size of their breasts to alleviate shoulder, neck and back symptoms. Breast tissue is resected to reduce volume but also requires a reduction in the breast skin envelope with extensive surgical incisions. Without reduction of the skin envelope of the breast, severe ptosis (droopiness) of the breast will occur.

Another example is liposuction which may aggravate elastosis because the soft tissue content is reduced without reduction in the surface area of the skin envelope. The degree of esthetic contour reduction is limited by the preexisting looseness of the skin envelope. Typically, liposuction involves the removal of subcutaneous fat through a suction cannula inserted through the skin surface. Excess suctioning of fat will aggravate any preexisting elastosis. Any other modality that reduces subcutaneous fat through dieting or ablation of fat cells is likely to aggravate a preexisting elastosis if a concomitant reduction of the skin envelope does not occur. This is especially true in the hip and thigh area where a condition called "cellulite" is due to a preexisting looseness of skin. Many patients have a more severe looseness of skin in the hip and thigh area that would be aggravated by any fat removal. Skin tightening procedures that involve large surgical incisions result in severe scarring to the thigh and hip area that are a poor tradeoff to any esthetic contour reduction.

There is a need for a method and apparatus to achieve skin tightening without major surgical intervention. There is a further need for a method and apparatus to achieve skin tightening by the controlled remodeling of collagen in the skin and underlying fibrous partitions of the subcutaneous fat. Still a further need exists to tighten a skin envelop with minimal skin or underlying subcutaneous tissue cell necrosis. Yet another need exists to provide a method and apparatus for the controlled remodeling of collagen in tandem with subcutaneous fat ablation in which a net tightening of the skin envelope occurs with an esthetic contour reduction.

SUMMARY OF THE INVENTION

Accordingly, an object of the invention is to provide a method and apparatus to tighten skin.

Another object of the invention is to provide a method and apparatus to tighten skin without major surgical intervention.

Yet another object of the invention is to provide a method and apparatus to tighten skin with controlled remodeling of collagen.

A further object of the invention is to provide a method and apparatus that delivers a mechanical force and electromagnetic energy to a tissue site to change a skin surface.

A further object of the invention is to provide a method and apparatus that delivers a mechanical force and electromagnetic energy to a tissue site to change the contour of a soft tissue structure.

These and other objects of the invention are achieved in an apparatus to modify a skin surface or a soft tissue structure underlying the skin surface. A template has a soft tissue mechanical force application surface. The mechanical force application surface is configured to apply pressure to the soft tissue structure. An energy delivery device is coupled to the template. The energy delivery device is configured to deliver sufficient energy to the template to form a template energy delivery surface.

In one embodiment, a template means is configured to apply the mechanical force to the soft tissue structure at the mechanical force application surface. An energy delivery means is coupled to the template means and provides a controlled delivery of electromagnetic energy to the skin surface that does not exceed 1,000 joules/sec/cm2 during a single treatment session. A combination of the mechanical force and the controlled delivery of electromagnetic energy changes a contour of the soft tissue structure.

In another embodiment, a method of operating an apparatus for modifying a structure provides an apparatus that includes a template means configured to receive a structure and apply a mechanical force. The apparatus also includes an energy delivery means coupled to the template means to provide a controlled delivery of electromagnetic energy to the structure not exceeding a dose rate of 10 joules/cm2. Sufficient mechanical force and electromagnetic energy is delivered to the structure to remodel at least a portion of the structure.

The mechanical force application surface can be a positive pressure application surface that applies compression to the soft tissue structure or a negative pressure application surface that creates an extension of the soft tissue structure. Application of the mechanical force and delivery of the energy has a variety of different effects including but not limited to, (i) tightening the skin surface, (ii) smoothing the skin surface, (iii) improving a compliance of the skin surface, (iv) improving a flexibility of the skin surface, (v) remodeling of collagen in the soft tissue structure, (vi) cleaving collagen cross-links to remodel collagen, (vii) remodeling of collagen in the soft tissue structure with reduced cell necrosis, (viii) cleaving collagen cross-links and contracting a longitudinal axis of a collagen fibril, (ix) cleave collagen cross-links and extend a longitudinal axis of a collagen fibril, (x) cleaving collagen cross-links and shearing of a collagen fibril matrix, (xi) directing converging and diverging mechanical forces to the skin surface to smooth the skin surface and tighten the skin surface, (xii) directing converging and diverging mechanical forces to the soft tissue structure to create a three-dimensional contouring of the soft tissue structure, (xiii) creating a compressive force to collagen in the underlying soft tissue structure and (ix) delivering sufficient pressure and creating an extension force to collagen in the underlying soft tissue structure.

The mechanical force can, (i) create a compressive force to collagen in the underlying soft tissue structure, (ii) create an extension force to collagen in the underlying soft tissue structure and (iii) create a shearing force in the underlying soft tissue structure.

DETAILED DESCRIPTION

Figure 1:
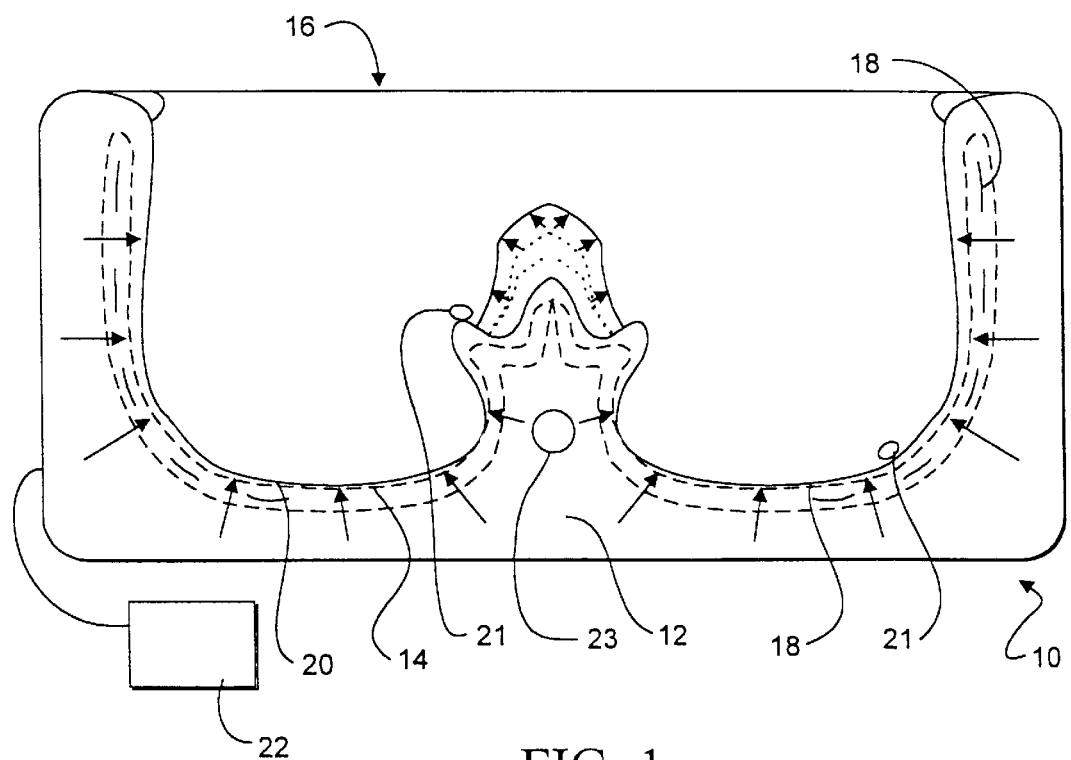
FIG. 1 is a cross-sectional view of a template of the present invention.
Figure 2:
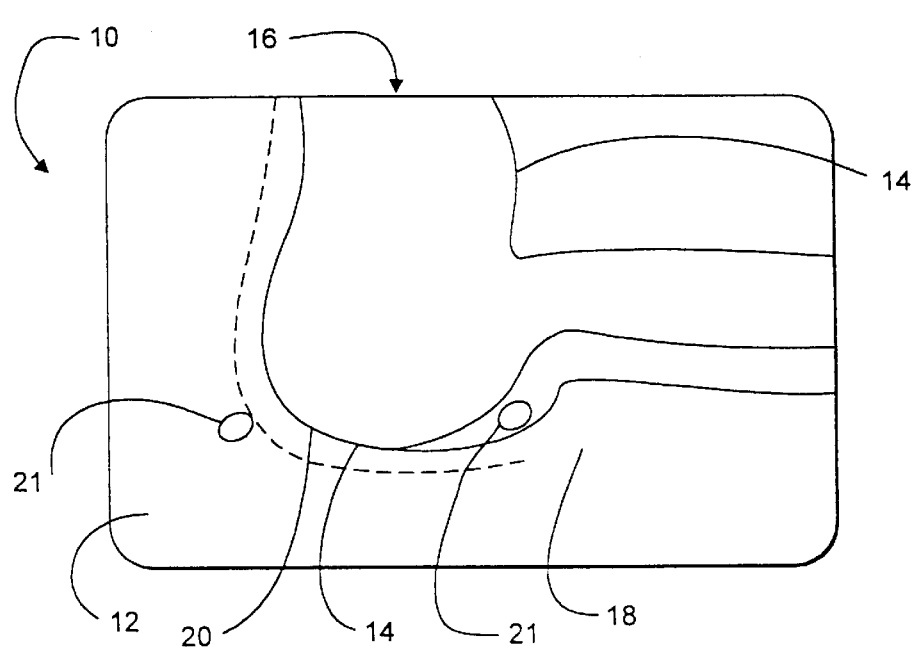
FIG. 2 is a lateral section view of the template illustrated in FIG. 1.

Referring now to FIGS. 1 and 2, an apparatus 10 to modify a skin surface or a soft tissue structure underlying the skin surface. A template 12 includes a soft tissue mechanical force application surface 14 and a receiving opening 16 to receive a body structure. Mechanical force application surface 14 is configured to receive the body structure and apply pressure to soft tissue in the body structure. An energy delivery device 18 is coupled to template 12. Energy delivery device 18 is configured to deliver sufficient energy to template 12 to form a template energy delivery surface 20 at an interior of template 12.

Mechanical force application surface 14 can apply pressure, suction, adhesion and the like in order to create an extension or compression of the soft tissue collagen containing structure and/or the skin surface.

Energy delivery device 18 and an energy source may be a single unit or each can be separate. Suitable energy sources 22 include but not limited to, resistive heating, RF, coherent and incoherent light, microwave, electrical, thermal, magnetic, frictional heating, ultrasound, liquid thermal jet and cryogenic fluids. Energy delivery device 18 can form an energy delivery surface 20 in template 12 which can be the same size as mechanical force application surface 14.

Template 12 applies both a mechanical force and delivers energy to, (i) tighten the skin, (ii) smooth the surface of the skin, (iii) improve a compliance of the skin surface, (iv) improve a flexibility of the skin surface and (v) provides cellular remodeling of collagen in soft tissue anatomical structures. Mechanical force application surface 14, (i) is at least partially conforming to the skin surface, (ii) may apply a substantially even pressure to the soft tissue anatomical structures and (iii) can apply a variable pressure to the skin surface and underlying soft tissue structures. The combined delivery of electromagnetic energy and a mechanical force is used to create a three-dimensional contouring of the soft tissue structure. The amount of mechanical force applied by mechanical force application surface 14, (i) is sufficient to achieve a smoothing effect of the skin surface, (ii) can be less than the tensile strength of collagen in tissue and (iii) is sufficient to create vectors that cleave collagen cross-links to remodel collagen containing structures.

Template 12 can include a reverse thermal gradient device 23 which may be a closed loop cooling channel positioned in the interior of template 12. Reverse thermal gradient device can be positioned at mechanical force application surface 14.

A sensor 21 is positioned at template energy delivery surface to monitor temperature, impedance and the like. Suitable sensors 21 include impedance and thermal devices. Sensor 21 is used to control the delivery of energy and reduce the chance of cell necrosis at the surface of the skin as well as damage to underlying soft tissue structures. Sensor 21 is of conventional design, including but not limited to thermistors, thermocouples, resistive wires, and the like. A suitable thermal sensor 21 includes a T type thermocouple with copper constantene, J type, E type, K type, fiber optics, resistive wires, thermocouple IR detectors, and the like.

Apparatus 10 is designed for the specific energy requirements of each type of bond within the collagen matrix. Collagen crosslinks may be either intramolecular (hydrogen bond) or intermolecular (covalent and ionic bonds). Hydrogen bonds are disrupted by heat. Covalent bonds may be cleaved with the stress created from the hydrogen bond disruption and the application of an external mechanical force. Cleavage of ionic bonds may be achieved with an alternating electrical moment in addition to the application of an external mechanical force that is applied by template 12. The strength of a hydrogen bond is relatively weak and can be thermally disrupted without ablation of tissue. The in vitro thermal cleavage of the hydrogen bond crosslinks of tropocollagen can result in the molecular contraction of the triple helix up to one third of its original length. However, in vivo collagen exists in fibrils that have extensive intermolecular crosslinks that are covalent or ionic. These covalent and ionic crosslinks are stronger and cannot be easily disrupted with heat. These intermolecular bonds are the main structural determinants of matrix strength and morphology. In vivo thermal disruption of intramolecular hydrogen bonds will not by itself result in a significant change in matrix morphology. As the intermolecular crosslinks are heat stable, cleavage may occur by a secondary process which can be the result of thermal disruption of intramolecular hydrogen bonds. In the non-polar region of the collagen fibril, intermolecular covalent bonds predominate (intramolecular covalent bonds are also present but are fewer in number).

Figure 3:
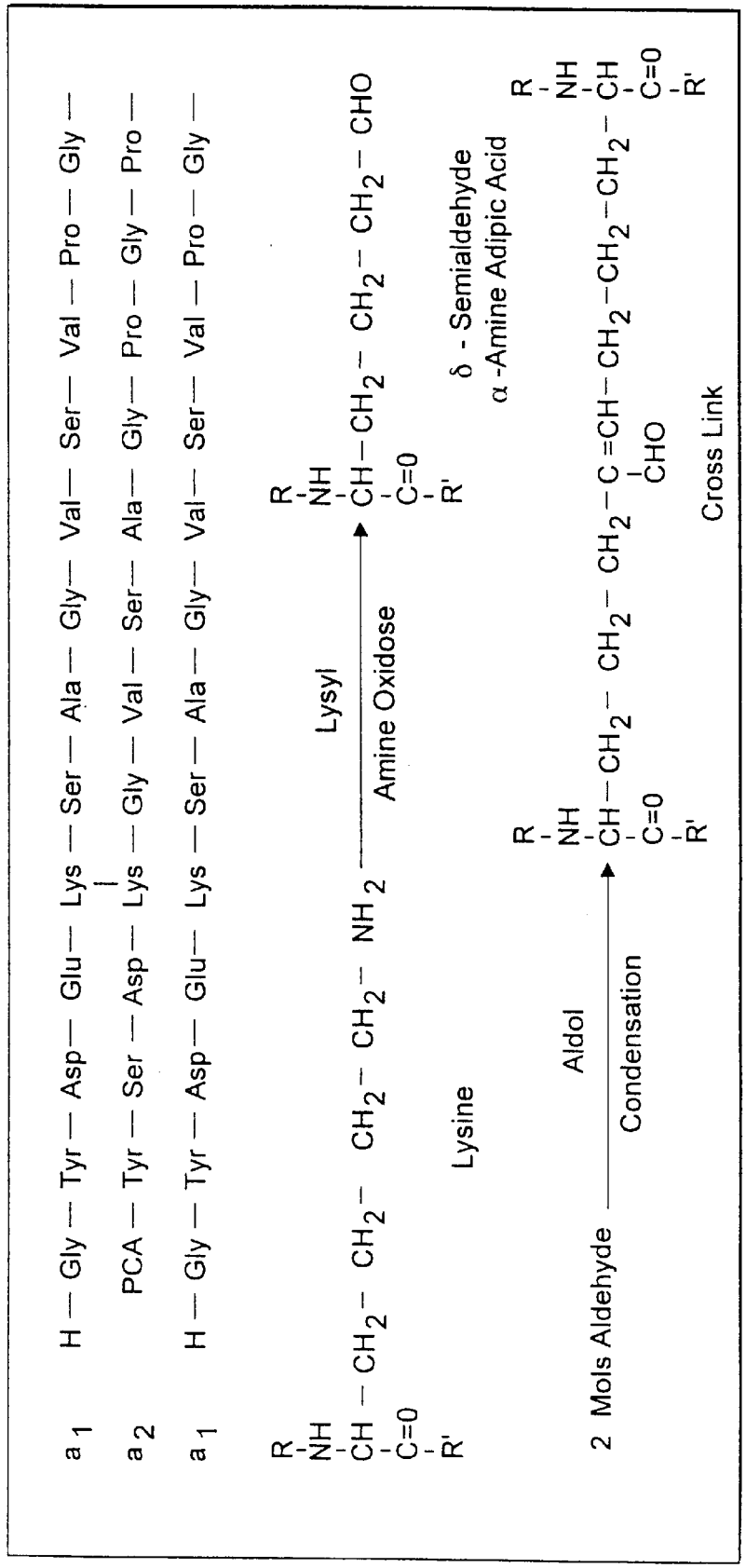
FIG. 3 illustrates intramolecular cross-inking of collagen.
Figure 4:
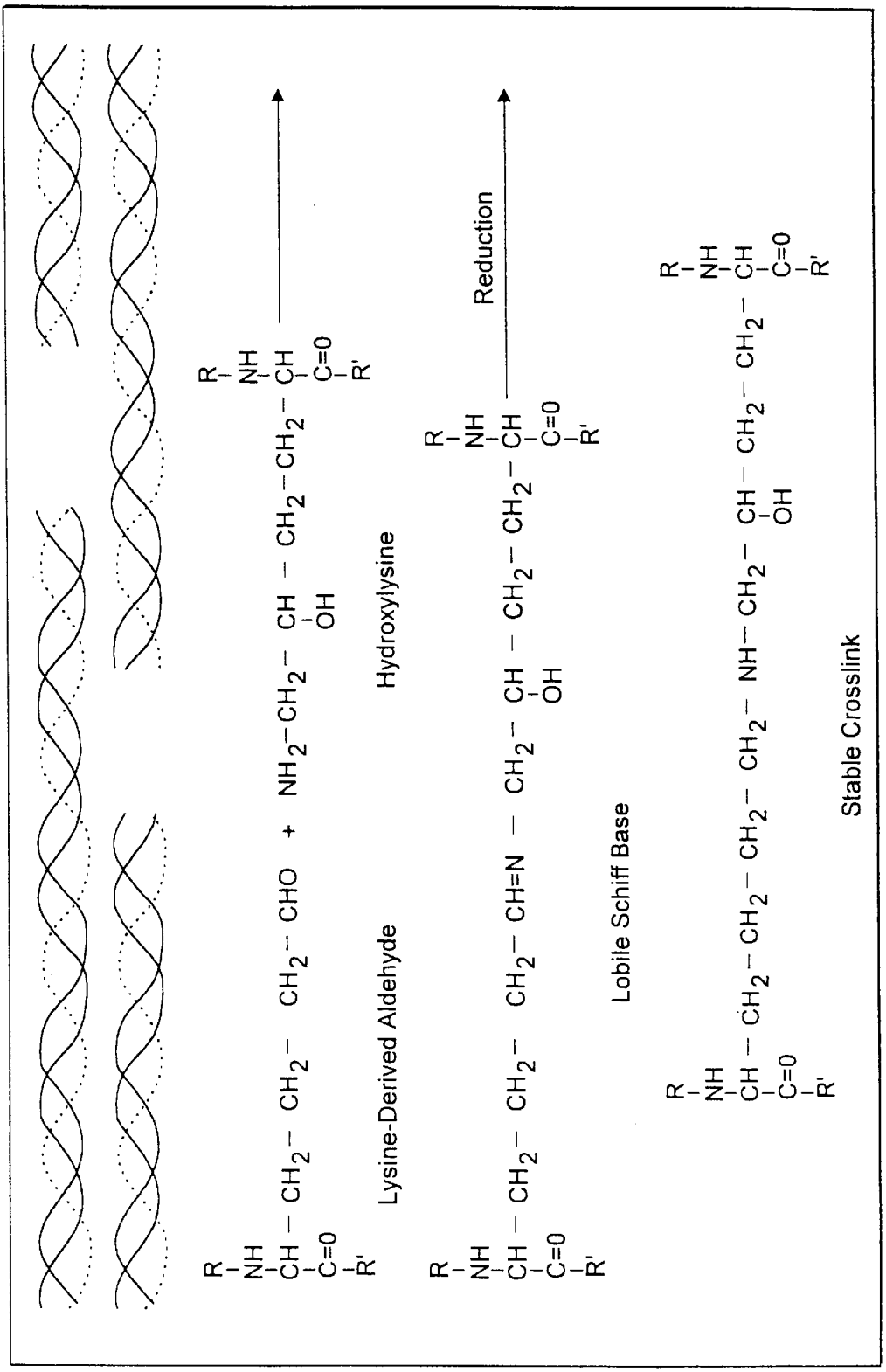
FIG. 4 illustrates intermolecular cross-linking of collagen.

These intermolecular covalent crosslinks increase with age, see FIGS. 3 and 4. As a result, the solubility of the collagen matrix in a soft tissue structure is reduced with this maturation process. Although tensile strength is increased, the collagen containing tissue becomes less compliant. Cleavage of an intermolecular bond requires approximately 1 et of energy and can not be accomplished by heat without thermal ablation of tissue. In addition, covalent bonds are not strongly polar and will not be significantly affected by an RF current at this reduced power level. Cleavage of intermolecular covalent bonds that result in matrix remodeling without ablation is achieved by the stress created from the thermal disruption of intramolecular hydrogen bonds. Additional remodeling stress can be provided with the application of an external force that has the appropriate orientation to the fibrils of the matrix. Ionic bonds are essentially intermolecular and are present in the polar regions of the fibril. Although slightly weaker than covalent bonds, thermal disruption cannot occur without ablation of tissue. An RF field is an effective means to cleave these bonds and is created by the an in phase alternating ionic motion of the extracellular fluid. Frequency modulation of the RF current may allow coupling to the ionic bonds in the polar regions of the fibril. Remodeling of a target site may be optimized by the selection of a band of the spectrum that is target site specific in order to reduce collateral damage. If an optimized intrinsic absorption is insufficient then a selective medium may be provided to alter the absorption in order to discriminate various soft tissue structures. This may be achieved by altering the absorption. By altering the extra-cellular fluid content of a soft tissue in specific ways, the delivery of energy to a target tissue site is achieved with minimal damage to collateral structures such as skin and adjacent soft tissue structures.

The reforming of bonds at the same bond sites will diminish the remodeling process. Relaxation phenomena may inhibited with the application of an external mechanical force that separates bond sites but allows the reforming of these covalent and ionic bonds in a lengthened or contracted morphology. This can be the underlying biophysical process that occurs with the controlled remodeling of the collagen matrix. Ground substance may also function to diminish relaxation of crosslinks through competitive inhibition. Chondroitin sulfate is a highly charged molecule that is attached to a protein in a "bottle brush" configuration. This configuration promotes attachment at polar regions of the fibril and reduces the relaxation of ionic bonds in this region. As a consequence, immature soluble collagen, which has fewer intermolecular crosslinks and contains a higher concentration of ground substance, may be more easily remodeled. The induction of scar collagen through the wound healing sequence may also facilitate the remodeling process within a treatment area.

The cleavage of a collagen crosslink requires has an energy threshold. Collagen cleavage in tissue is a probability event. There is a greater probability that a collagen bond will be cleaved with higher temperatures. Cleavage of collagen bonds will occur at lower temperatures but at a lower frequency. Low level thermal cleavage is frequently associated with relaxation phenomena in which there is not a net change in molecular length. An external force that mechanically cleaves the fibril may reduce the probability of relaxation phenomena. The application of an external force will also provide a means to lengthen or contract the collagen matrix at lower temperatures while reducing the potential of surface ablation. The cleavage of crosslinks with collagen remodeling may be occurring at a basal metabolic temperature that is expressed morphologically as the process of aging. Although the probability for significant cleavage in a short period of time is small, aging may be expressed as a low level steady state of collagen remodeling with the external force of gravity that becomes very significant over a period of decades. Hydrogen bonds which are relatively weak (0.2 ev to 0.4 ev) are formed within the tertiary structure of the tropocollagen molecule.

Figure 5:
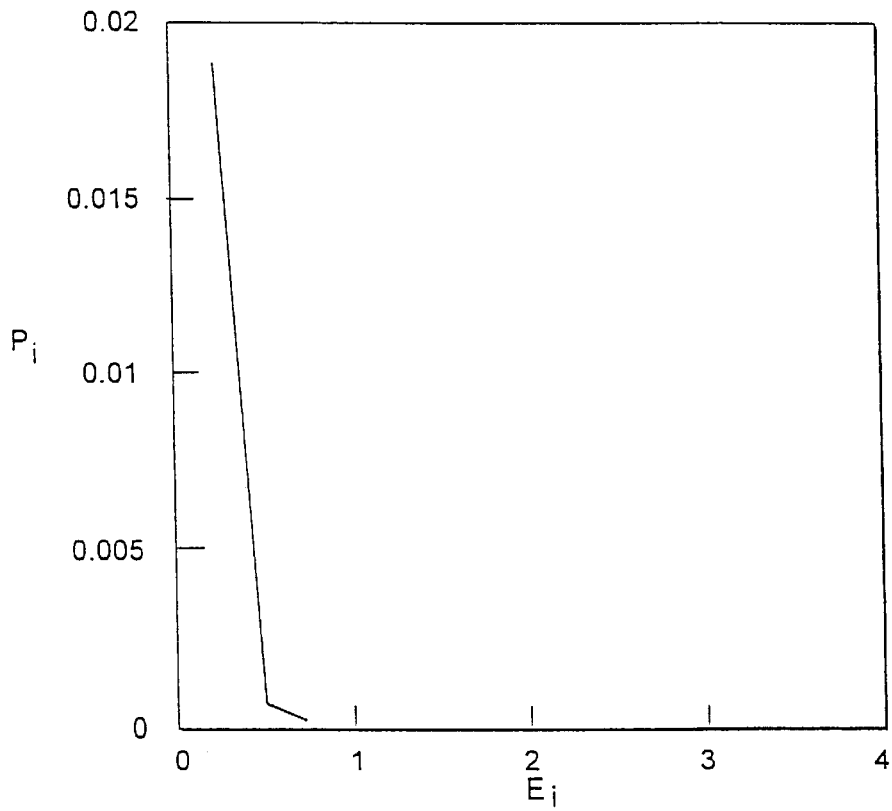
FIGS. 5 and 6 are two graphs illustrating a probability of collagen cleavage with changing bond strength at 37 degrees C.
Figure 6:
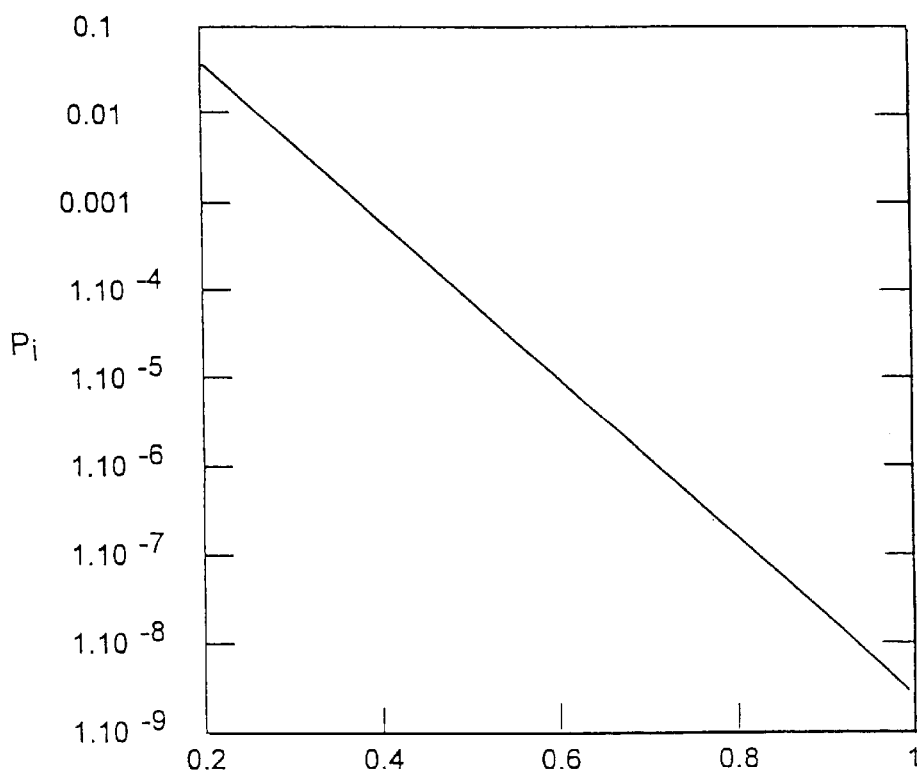

Thermal disruption of these bonds can be achieved without ablation of tissue, i.e., cell necrosis. The probability of hydrogen bond disruption at a certain temperature can be predicted by statistical thermodynamics. If a Boltzmann distribution is used to calculate the probability of bond disruption then a graph illustrating the relationship between bond strength and the probability of bond disruption at a certain temperature can be produced. Graphs of the probability of cleavage at 37 degrees centigrade with various bond strengths are shown in FIGS. 5 and 6.

Different morphological expressions of aging may be due to the effect of gravity upon the matrix of a particular area. In areas of the skin envelope in which gravity lengthens the matrix, elastosis of skin will occur. In contrast to skin aging certain anatomical structures, such as joint ligaments, will appear to "tighten" with the aging process. The reduced range of motion may be due in part to the vertical vector of gravity contracting the matrix of a vertically aligned ligament. However, most of the "tightening" or reduced range of motion of joints may not be secondary to a contracted matrix but is due to reduced flexibility of the matrix caused by increased intramolecular cross-linking that occurs with aging. Essentially, the controlled remodeling of collagen is the reversal of the aging process and involves the reduction in the number of intermolecular crosslinks. As a result the remodeled matrix becomes less brittle. Greater flexibility of the soft tissue has several functional advantages including an increased range of motion of component joints.

When the rate of thermal cleavage of intramolecular crosslinks exceeds the rate of relaxation (reforming of hydrogen bonds) then the contraction of the tertiary structure of the molecule can be achieved. No external force is required for this process to occur. Essentially, the contraction of the tertiary structure of the molecule creates the initial intermolecular vector of contraction. The application of an external mechanical force during thermal cleavage will also affect the length of the collagen fibril and is determined by the overall sum of intrinsic and extrinsic vectors that is applied during a cleavage event. Collagen fibrils in a matrix exhibit a variety of spatial orientations. The matrix is lengthened if the sum of all vectors act to distract the fibril. Contraction of the matrix is facilitated if the sum of all extrinsic vectors acts to shorten the fibril. Thermal disruption of intramolecular bonds and mechanical cleavage of intermolecular crosslinks is also affected by relaxation events that restore preexisting configurations. However, a permanent change of molecular length will occur if crosslinks are reformed after lengthening or contraction of the collagen fibril. The continuous application of an external mechanical force will increase the probability of crosslinks forming alter lengthening or contraction of the fibril.

The amount of (intramolecular) hydrogen bond cleavage required will be determined by the combined ionic and covalent intermolecular bond strengths within the collagen fibril. Until this threshold is reached little or no change in the quaternary structure of the collagen fibril will occur. When the intermolecular stress is adequate, cleavage of the ionic and covalent bonds will occur. Typically, the intermolecular cleavage of ionic and covalent bonds will occur with a ratcheting effect from the realignment of polar and nonpolar regions in the lengthened or contracted fibril. The birefringence (as seen with the electron microscope) of the collagen fibril may be altered but not lost with this remodeling process. The quarter staggered configuration of the tropocollagen molecules in the native fiber exhibits a 680 Å banding which either lengthens or contracts depending on the clinical application. The application of the mechanical force with template 12 during the remodeling process determines if a lengthen or contracted morphology of the collagen fibril is created. An external force of contraction will result in the contraction of the tertiary and quaternary structure of the matrix. With the application of an external distraction force, intramolecular contraction may still occur from the intrinsic vector that is inherent within its tertiary structure. However, overall lengthening of the quaternary structure of the fibril will occur due to the mechanical cleavage of the intermolecular bonds. Contraction of the tertiary structure with overall lengthening of the collagen fibril can alter the birefringence of the matrix. The altered periodicity will be exhibited in the remodeled matrix that will correlate to the amount of lengthening achieved.

Delivery of both electromagnetic energy and mechanical energy to the selected body structure involves both molecular and cellular remodeling of collagen containing tissues. The use of low level thermal treatments over several days provides an additional way to contract skin with minimal blistering and cell necrosis. Cellular contraction involves the initiation of an inflammatory/wound healing sequence that is perpetuated over several weeks with sequential and lengthy low level thermal treatments. Contraction of skin is achieved through fibroblastic multiplication and contraction with the deposition of a static supporting matrix of nascent scar collagen. This cellular contraction process is a biological threshold event initiated by the degranulation of the mast cell that releases histamine. This histamine release initiates the inflammatory wound healing sequence.

Molecular contraction of collagen is a more immediate biophysical process that occurs most efficiently with electromagnetic energy delivery devices, including but not limited to RF electrodes. The clinical setting is physician controlled and requires more precise temperature, impedance, and energy delivery monitoring to avoid blistering of the skin. Measured impedance will vary with the frequency of the electromagnetic energy applied to the skin surface and/or underlying soft tissue structure.

Patients may be treated with one or both modalities to achieve the optimal esthetic result. Refinements to the treatment area may be required using apparatus 10 in the physician's office.

Figure 7:
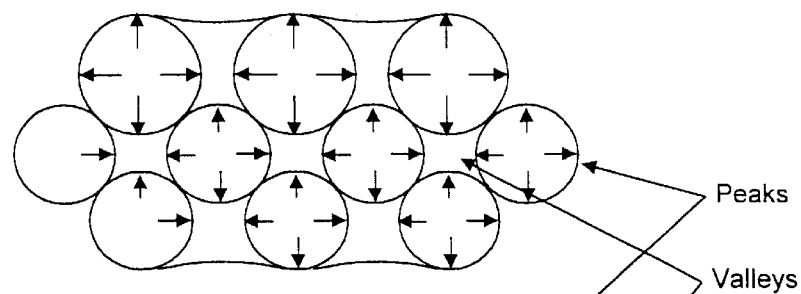
FIG. 7 is a top down view of a skin surface, illustrating the peaks and valleys of the surface and the vectors applied to the surface by the application of a mechanical force.
Figure 8:
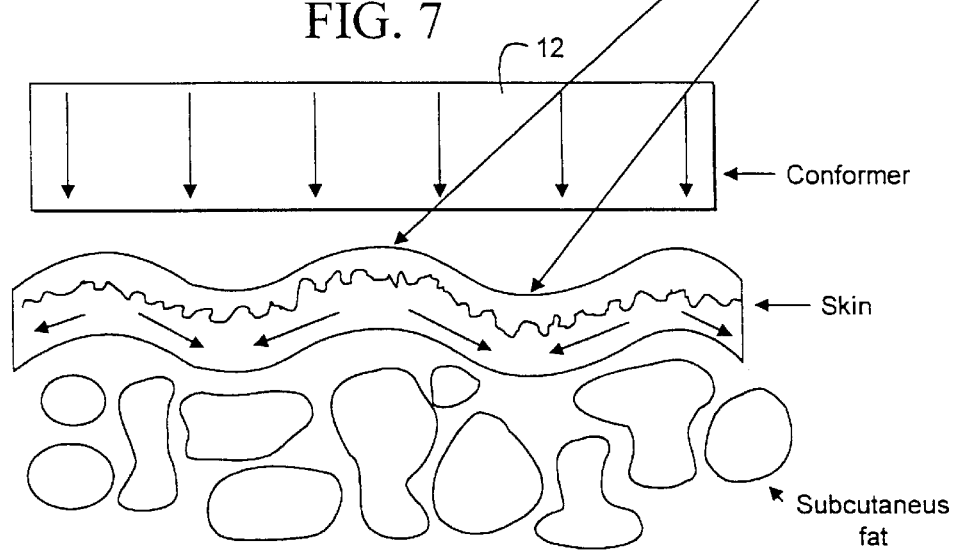
FIG. 8 is a cross-sectional view of the skin surface illustrated in FIG. 7.

However, tightening of a skin surface may accentuate any preexisting contour irregularities. For this reason, conforming esthetic template 12 is used to smooth surface contour irregularities. Essentially, the application of a mechanical force upon the collagen matrix involves both contraction or distraction of the selected soft tissue structure to achieve a smoother contour. Thermal (or em) cleavage of collagen crosslinks when combined with a mechanical force creates vectors that contract, distract or shear the longitudinal axis of the fibril. A vector space is created with the combination of a scalar component (heat) and a vector (an externally applied mechanical force). The vectors within this vector space vary depending upon the specific morphology. For example, the peaks and valleys of cellulite will have different vectors when uniform external compression is applied. As illustrated in FIGS. 7 and 8, template 12 produces converging and diverging vectors that smooth surface morphology by contracting (valleys) and distracting (peaks) the collagen matrix in a soft tissue structure. Diverging vectors on the peaks lengthen the collagen matrix while converging vectors in the valleys contract and compact the collagen matrix. The overall result is the smoothing of an irregular skin surface.

Figure 9:
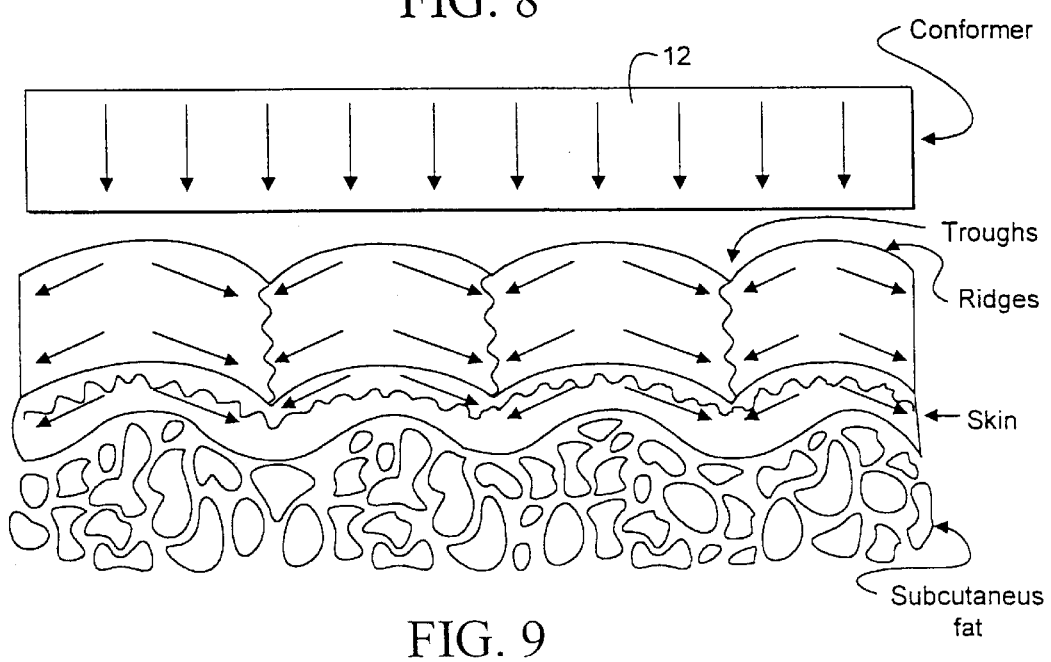
FIG. 9 is a cut-away view of the skin surface, with troughs and ridges, and underlying subcutaneous soft tissue.

Apparatus 10 may also be used to treat wrinkling of the skin. The treatment of skin wrinkles is shown in FIG. 9. In a skin wrinkle the vectors are directed perpendicular to the troughs and ridges of this contour deformity. Diverging vectors at the ridges of the skin converge in the trough of the wrinkle to smooth the surface morphology. The collagen matrix is distracted or extended at the ridges and contracted in the valleys. The overall result is the smoothing of the wrinkled skin surface.

Linear scars exhibit a similar morphology and can be remodeled with apparatus 10. Any surface irregularity with depressions and elevations will have vectors directed to the lowest point of the deformity. Prominent "pores" or acne scaring of the skin have a similar pattern to cellulite but on a smaller scale and can also be treated with apparatus 10. Clinically, the application of the mechanical force reduces the power required to remodel the matrix and diminishes cell necrosis of the skin surface as well as underlying soft tissue structures. Compression alters the extracellular fluid of the soft tissue structure (collagen) and exerts electrical impedance and thermal conductivity effects that allow delineation of a conduit-treatment interface of the collagen containing tissues. A deeper dermal interface will contract skin and exert three dimensional contour effects while a more superficial interface will smooth surface morphology.

Figure 10B:
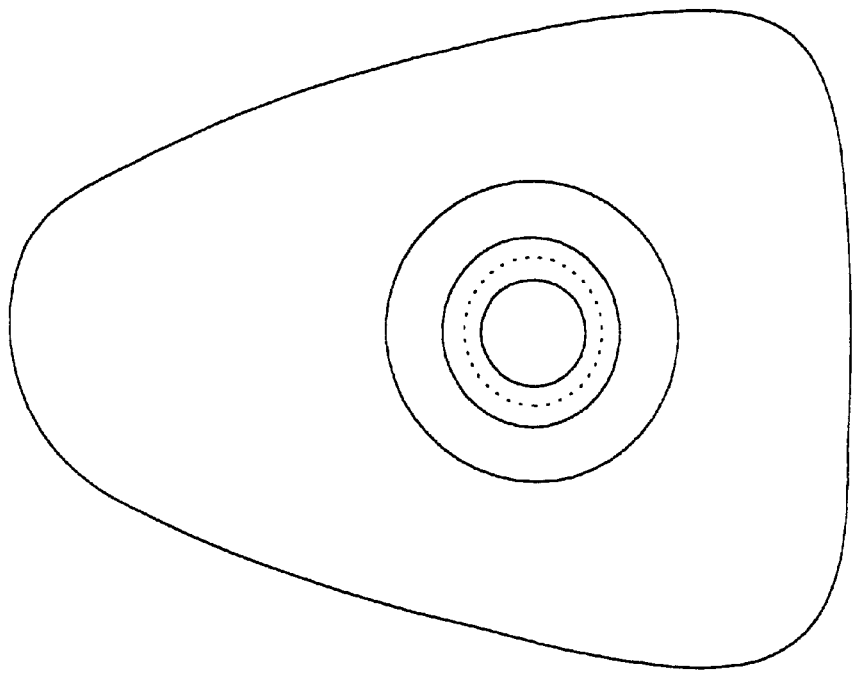
FIG. 10(b) is a front perspective view of the breast expander of FIG. 10(a).
Figure 10A:
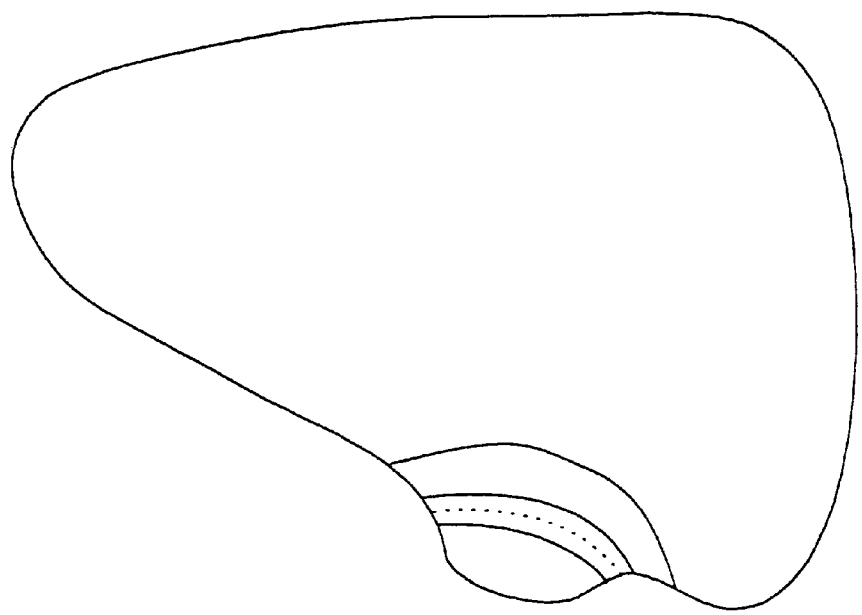
FIG. 10(a) is a lateral perspective view of a telescoping segment of a breast expander useful with the apparatus of FIG. 1.
Figure 10C:
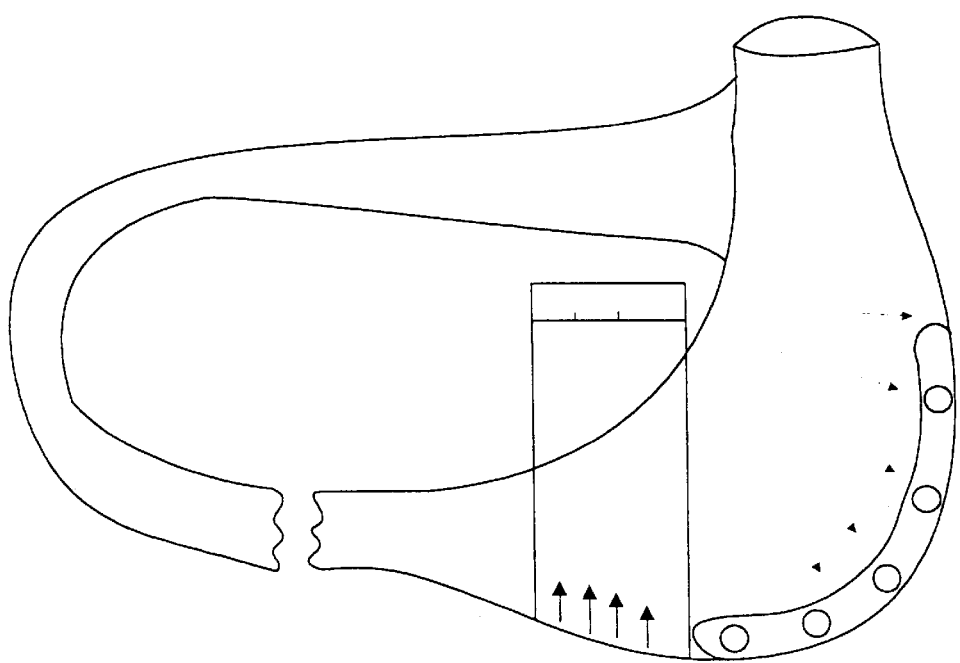
FIG. 10(c) illustrates a bra which functions as the template of FIG. 1.

In circumstances in which expansion of the skin envelope is needed, the combined application of heat and pressure is also required. For breast reconstruction, expansion of the skin envelope is typically achieved with each inflation of a subpectoral breast expander. FIGS. 10(a) and 10(b) illustrate an expander with an RF receiver electrode. A telescoping segment with an RF energy source is incorporated with access valve and is used to expand a nipple areolar donor site for Pectoralis "Peg" Procedure. The segmental expander can also be used to prepare the recipient site for delayed autologous "Peg" Flap. The pressure that is exerted on the skin and the periprosthetic scar capsule is from the inside. In this application, vectors are directed outward. As an adjunct to this expansion process, a controlled thermal pad may be incorporated into a bra, as illustrated in FIG. 10(c), which can be applied to the inferior pole of the breast skin to promote lengthening of collagen fibril within the skin and underlying scar capsule around the expander. The bra may also function as an external conforming template 12 to achieve a specific breast shape. The net result is the creation of a more esthetic breast reconstruction with three dimensional characteristics of the opposite breast. In a like manner, other garments can be utilized as external conforming templates for other anatomical body structures.

Figure 10E:
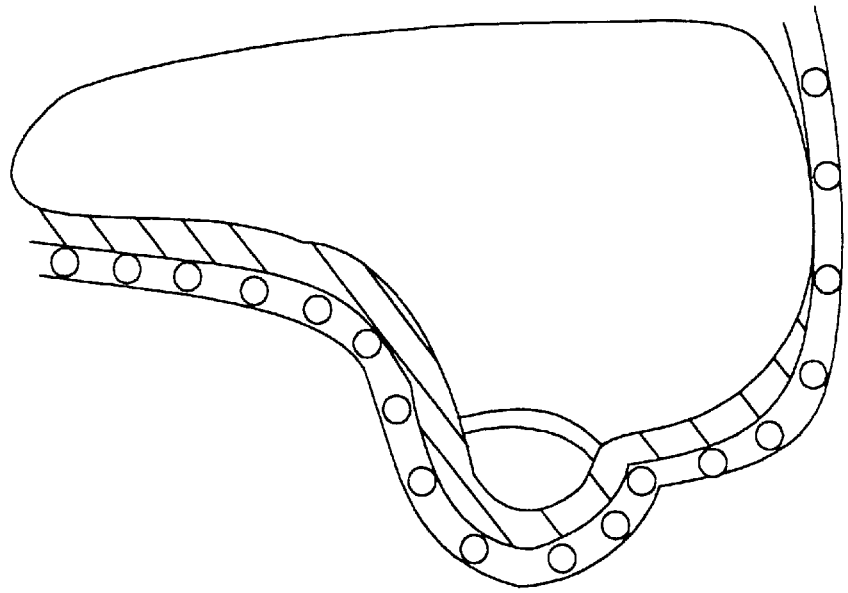
FIG. 10(e) is a lateral cross-sectional perspective view of a fully expanded breast expander within a breast.
Figure 10D:
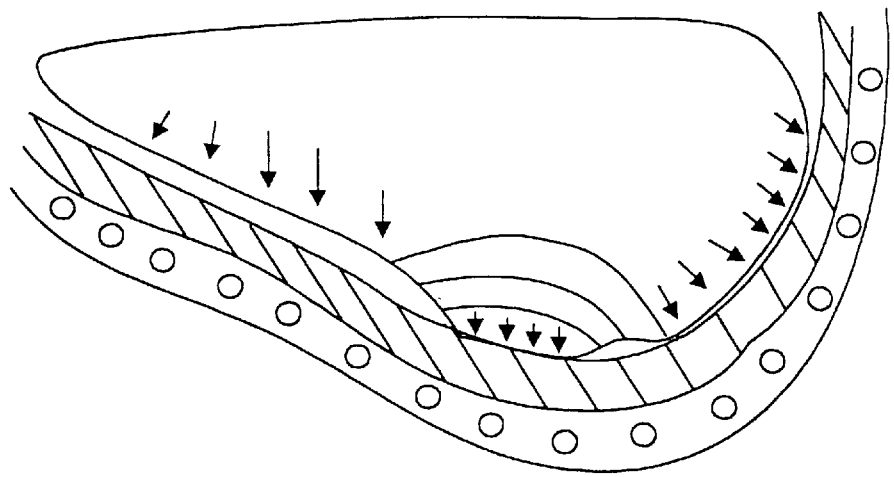
FIG. 10(d) is a lateral cross-sectional perspective view of a partially expanded breast expander within a breast.

In FIG. 10(d) a breast expander is partially expanded within the breast. In FIG. 10(e), the expander is fully expanded within the breast.

Figure 11:
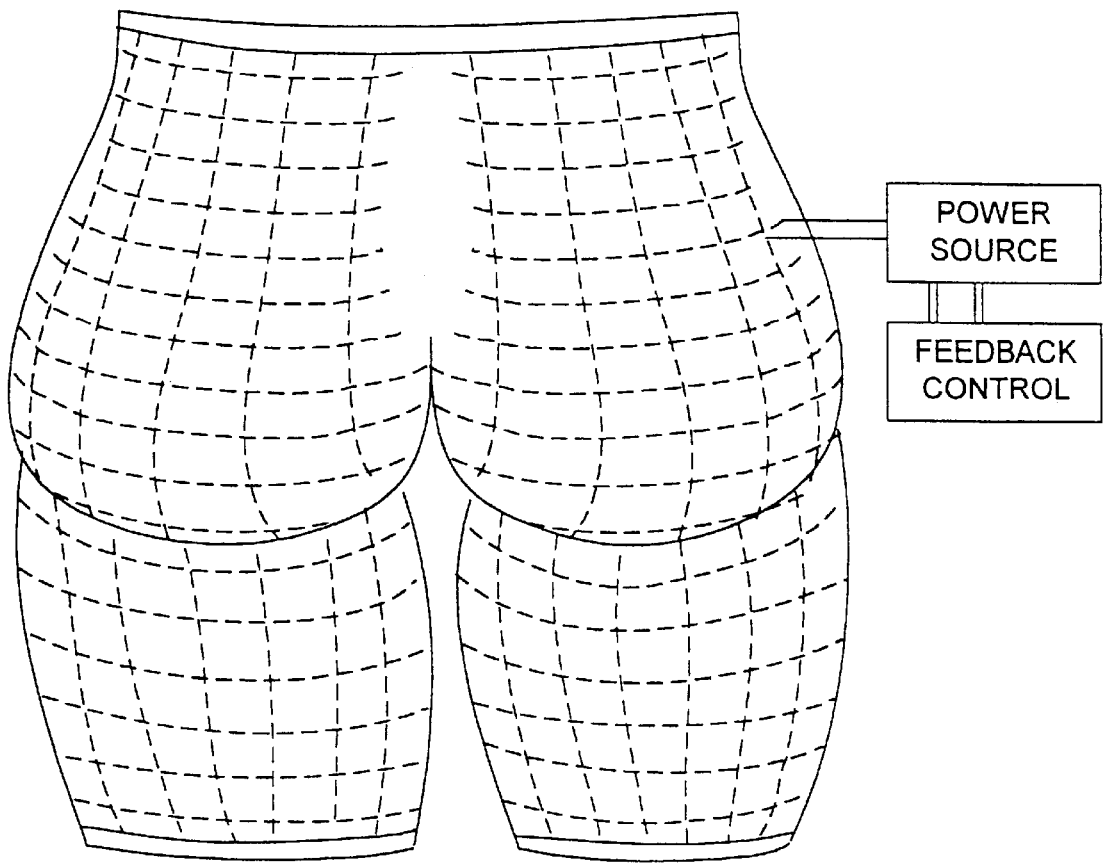
FIG. 11 illustrates a template in the form of a garment.

Template 12 applies a mechanical force in combination with the delivery of energy, with minimal cell necrosis to the skin surface and underlying soft tissue structure, to remodel collagen both esthetically and functionally. Template 12 can be in a variety of different forms including but not limited to a garment that is illustrated in FIG. 11. Energy source 22 can be directly incorporated into the fabric of a tight fitting garment or inserted as a heating/RF pad into a pocket of the garment. Another example of a garment is a tight fitting bra that extends over the arm and waistline with zone control that provides contraction of the skin of the breast, arms, and waistline to a variable amount to create a desired three-dimensional figure. Functional remodeling of collagen containing structures include a variety of different applications for aesthetic remodeling.

Figure 12A:
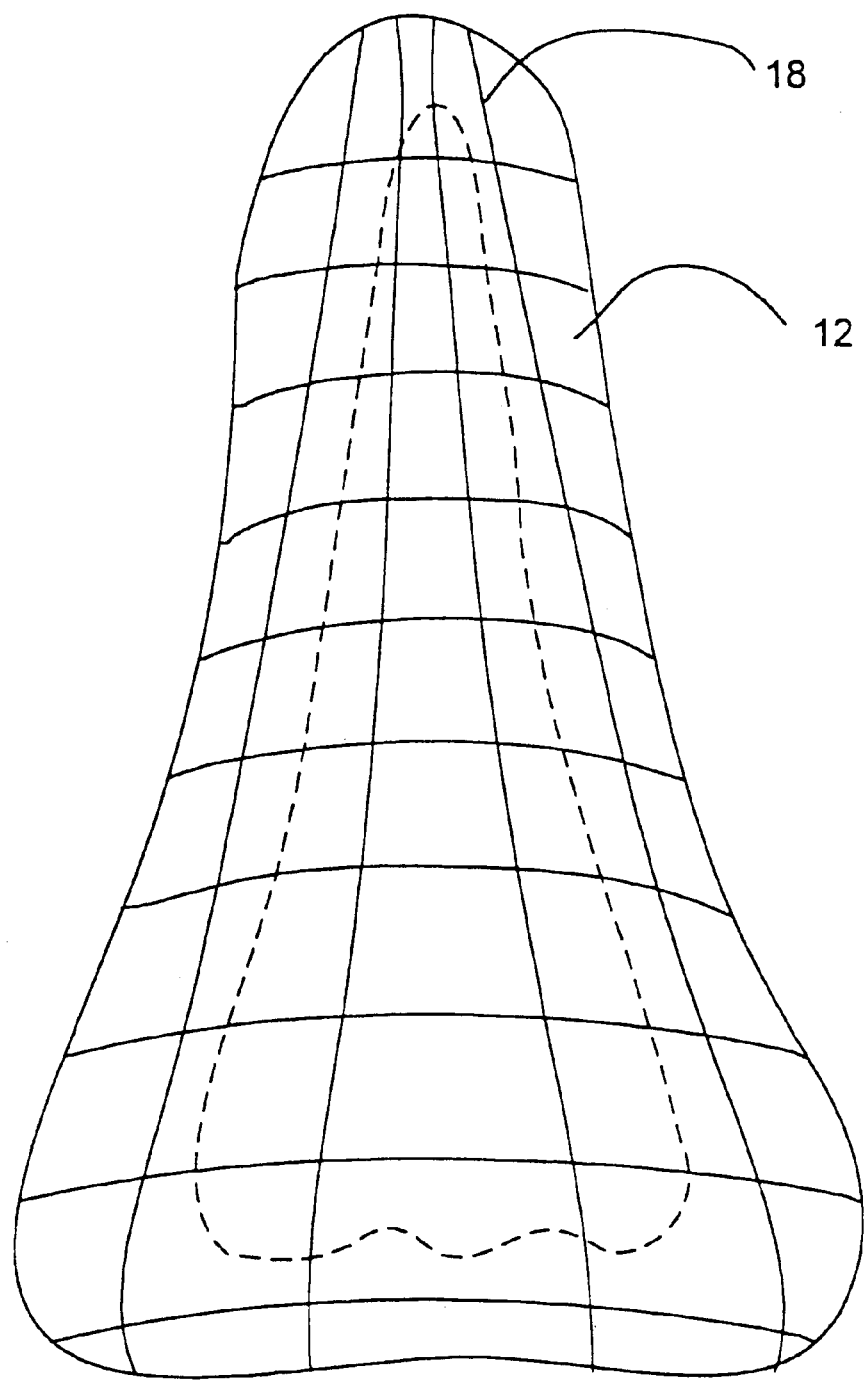
FIG. 12(a) illustrates a template that is positioned over a nose.
Figure 12B:
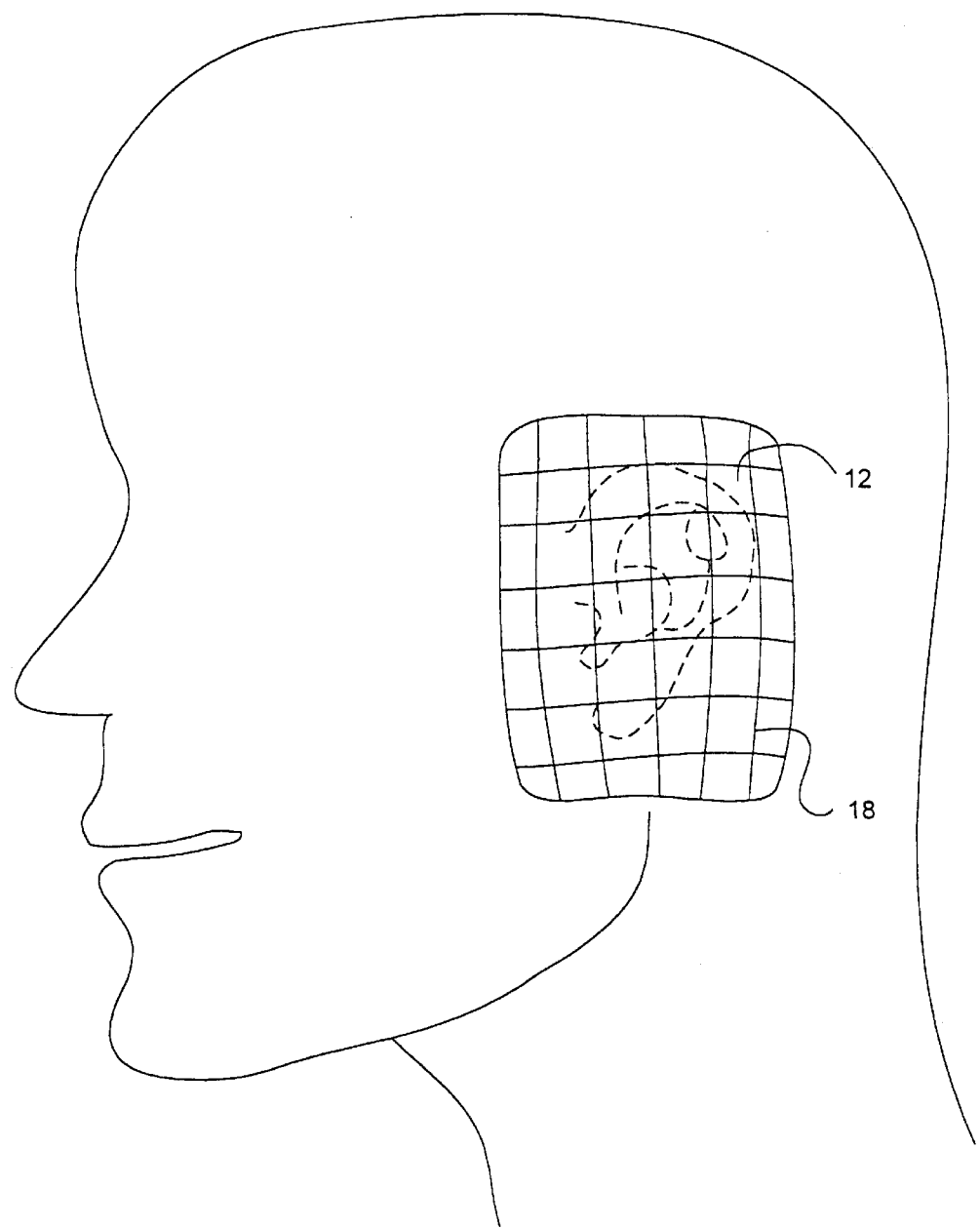
FIG. 12(b) illustrates a template that is positioned over an ear.

As shown in FIGS. 12(a) and 12(b), template 12 can be a garment positioned over the nose, a garment positioned around the ear, and the like.

Figure 13:
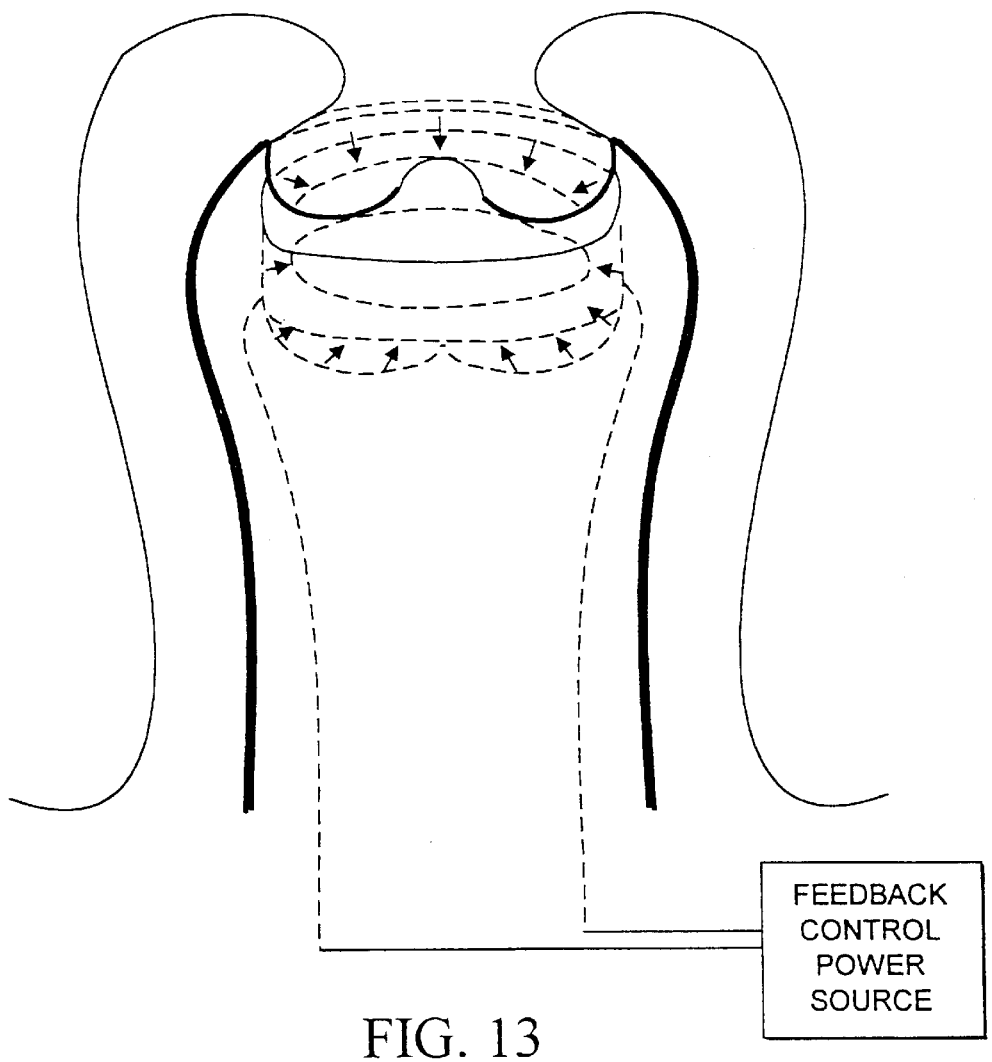
FIG. 13 is a perspective view of a template that is useful in the cervix.
Figure 14:
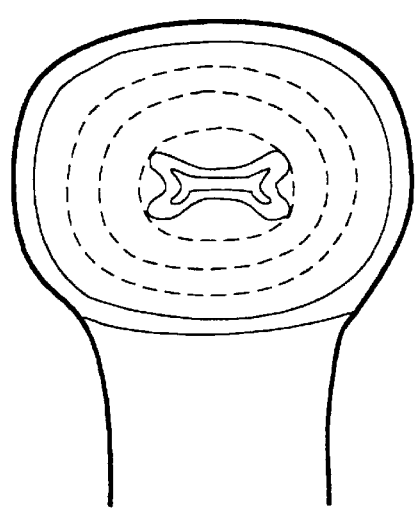
FIG. 14 is a cross-sectional view of the template of FIG. 13.

Template 12 can also be applied for functional purposes. Referring now to FIGS. 13 and 14, pre-term cervical dilation can be treated with a template 12 that is the impression "competent" cervix. The cervical template 12 create vectors that contract the circumference of the cervix. The incorporated energy delivery device 18 contracts the native matrix and induces scar collagen. The dilated cervical OS is tightened and the entire cervix is strengthened. Energy delivery device 18 can be incorporated into template 12 which can be the cervical conformer and inserted as a vaginal obturator. It will be appreciated that template 12 can be utilized for other functional treatments.

Figure 15A:
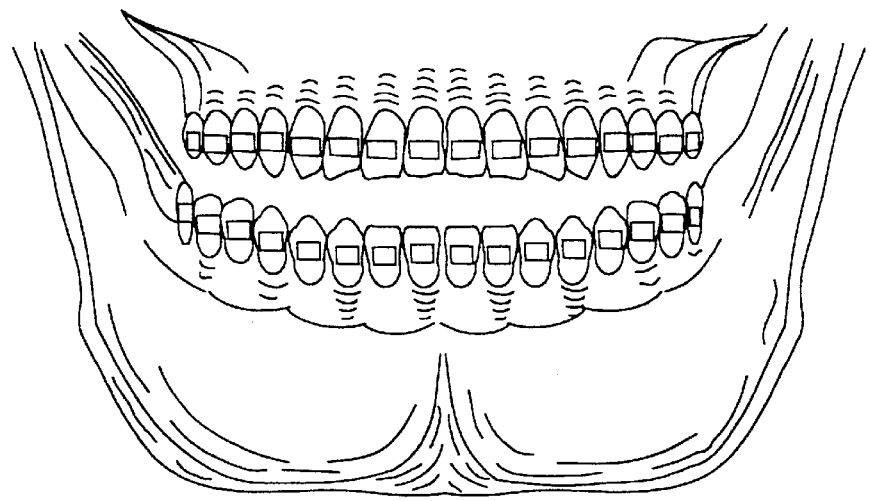
FIG. 15(a) is a front view of an orthodontic appliance that includes RF electrodes.
Figure 15B:
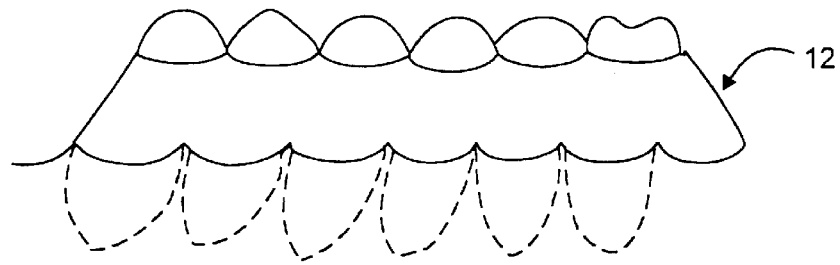
FIG. 15(b) is perspective view of an orthodontic appliance template of the device of FIG. 1.
Figure 15C:
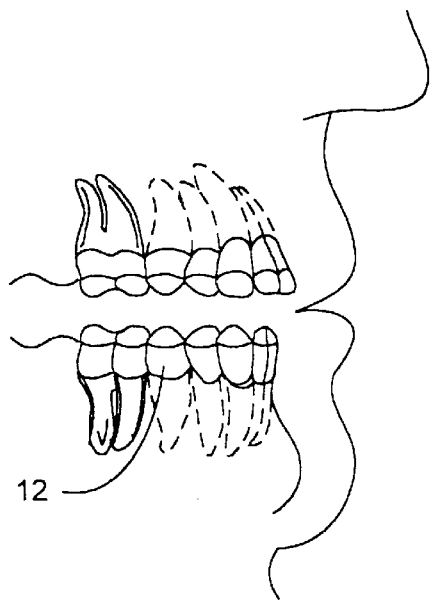
FIG. 15(c) is cross-sectional view of the template of FIG. 15(b).

In another embodiment, template 12 is a functional appliance that may be non conforming and can be separate or incorporated with the energy delivery device 18. Orthodontic braces that are designed with energy delivery device 18 are used to remodel dental collagen and apply rotation and inclination vectors on the neck of the tooth which is devoid of enamel. In FIG. 15(a) orthodontic braces are coupled to RF electrodes and associated power source. The orthodontic braces function as a non-conforming force application surface that is coupled to incorporated RF electrodes. FIGS. 15(b) and 15(c) illustrates a orthodontic appliance that is a conforming template 12 coupled to RF electrodes. As a consequence, orthodontic correction is more rapidly achieved than current modalities that employ only mechanical forces. Orthodontic correction can also be achieved with a conforming template 12 that is the corrected impression of the patient's dentition.

For orthopedic applications, an external fixation device is used as a non conforming functional appliance. This appliance is used in tandem with an energy source device, including but not limited to RF electrodes, that remodels the collagen of the callus tissue. More accurate alignment of osteotomy and fracture sites are possible with either a conforming or nonconforming brace that is used in tandem or is directly incorporated into energy delivery device 18. Improved range of motion of contracted joints and correction of postural (spinal) deformities can be achieved with this combined approach.

The ability to remodel soft tissue in anatomical structures other than skin is dependent upon the presence of preexisting native collagen. Induction of scar collagen is performed in tissue devoid or deficient of native collagen. Template 12 can be used to remodel the subcutaneous fat of hips and thighs in addition to the tightening of the skin envelope. The convolutions of the ear cartilage can be altered to correct a congenital prominence. The nasal tip can be conformed to a more esthetically pleasing contour without surgery.

Template 12 can be used with any modality that remodels collagen. In addition to RF (molecular) remodeling of collagen, cellular modalities that invoke the wound healing sequence can be combined with a conforming esthetic template. Thermal and chemical sources (glycolic acid) induce a low level inflammatory reaction of the skin. Scar collagen induction and fibroblastic (cellular) contraction are directed into converging and diverging vectors by a conformer that produces a smoother and tighter skin envelope. In addition to achieving a smoother and tighter integument, the texture of the skin is also improved with this remodeling process. Older or less compliant skin has a greater number of intermolecular crosslinks in the dermal collagen than younger skin. Scar collagen induction with cleavage of crosslinks will produce a softer and more compliant skin envelope.

Figure 16:
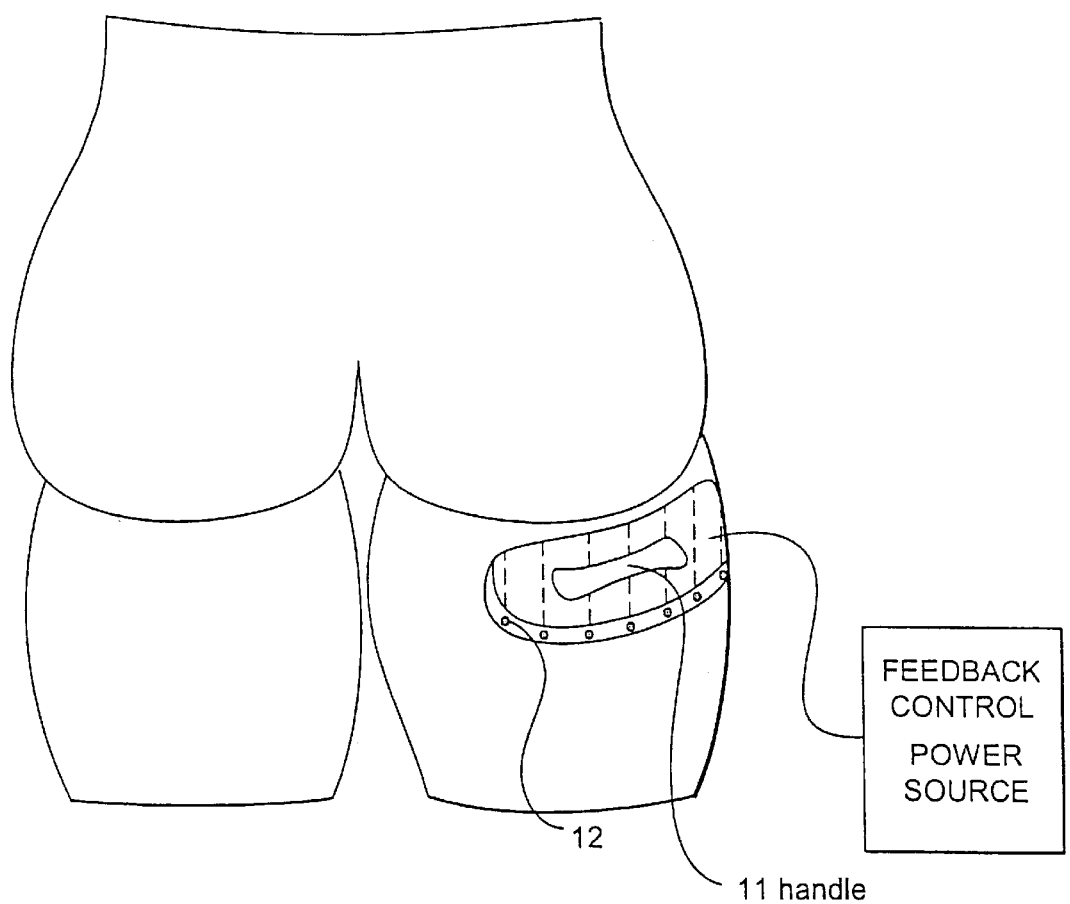
FIG. 16 illustrates a template made of a semisolid material that becomes more conforming to underlying soft tissue upon the application of a mechanical force.
Figure 17:
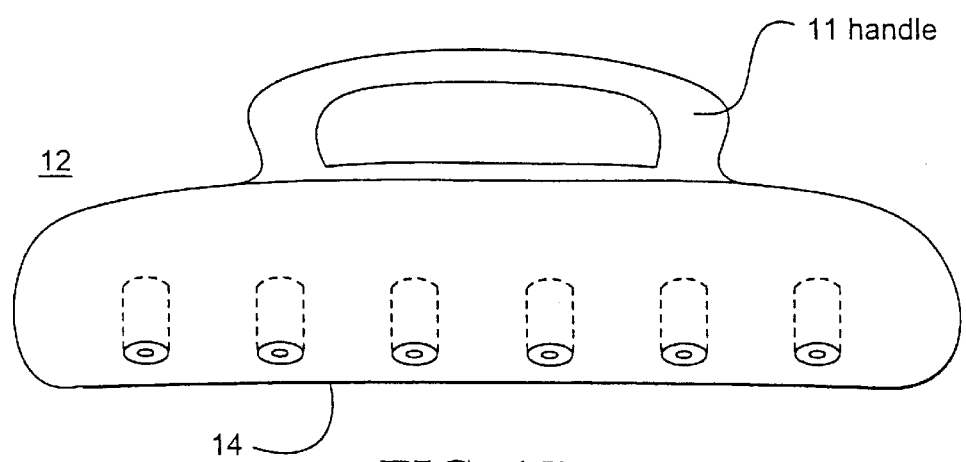
FIG. 17 illustrates a template with an adherent or suction mechanical force delivery surface that permits manual manipulation of skin and soft tissue structures.

Referring now to FIGS. 16 and 17, template 12 can be stationary or mobile. A hand held conforming template 12 that is mobile provides the practitioner with greater flexibility to remodel the collagen matrix. Pressure and impedance changes can serve as a guide for the manual application of template 12. A hand held template 12 with an incorporated energy source may be applied over a conductive garment that provides three dimensional conformance to the treatment area. Less accessible areas can be remodeled with this particular device. Template 12 of FIG. 16 is made of a semi-solid material that conforms a lax skin envelope to an underlying soft tissue structure. The semi-solid material customized the creation of force application surface 14 and reduces the need for precise fabrication of an esthetic template. Suitable semi-solid materials include soft plastics that are thermally and electrically conductive.

Controlled remodeling of collagen containing tissue requires an electromagnetic device that lengthens or contracts the matrix with a minimum of cell necrosis. Energy delivery device 18 can include a plurality of RF electrodes with or without insulation. The non-insulated sections of the RF electrodes collectively form template energy delivery surface 20. In a similar manner, microwave antennas, optical waveguides, ultrasound transducers and energy delivery or energy remove fluids are used to form template energy delivery surface 20. Individual electrodes and the like can be multiplexed and to provide selectable delivery of energy.

Template 12 delivers both electromagnetic energy and mechanical energy to the selected body structure. Suitable body structures include but are not limited to, hips, buttocks, thighs, calves, knees, angles, feet, perineum, the abdomen, chest, back flanks, waistline, legs, arms, legs, arms, wrists, upper arms, axilla, elbows, eyelids, face, neck, ears, nose, lips, checks, forehead, hands, breasts and the like.

A variety of different mechanical forces can be applied to tissue including but not limited to, (i) pressure, (ii) expansion, (iii) stretching, (iv) extension, (v) prolongation, or (vi) lengthening. The pressure force can be a positive pressure or a negative pressure. Positive pressure provides a compression of collagen containing tissue, with converging and diverging vectors, and negative pressure creates an extension of collagen containing tissue with converging and diverging vectors.

In various embodiments, energy delivery device 18 provides a controlled delivery of electromagnetic energy to the skin surface that does not exceed, 1,000 joules/cm2, or 10 joules/sec/cm2; provides a controlled delivery of electromagnetic energy to the skin surface not exceeding 600 joules/cm2 during a single treatment session (during a twenty-four hour period), operates in an impedance range at the skin surface, not exceeding 200 joules/cm2 during a single treatment session, or not exceeding 10 joules/sec/cm2; operates in an impedance range at the skin surface of, 70 ohms cm2 measured at a frequency of 88 Hz to 40 Kohms cm2 measured at a frequency of 10 KHz; provides a controlled delivery of electromagnetic energy to operate in a range of thermal conductivity at a skin surface of 0.21 to 0.60 k; operates in a range of compression force applied to the skin surface and/or the underlying soft tissue anatomical structure not exceeding 400 mmHg, not exceeding 300 mm, not exceeding 200 mmHg or not exceeding 100 mmHg.

Figure 18:
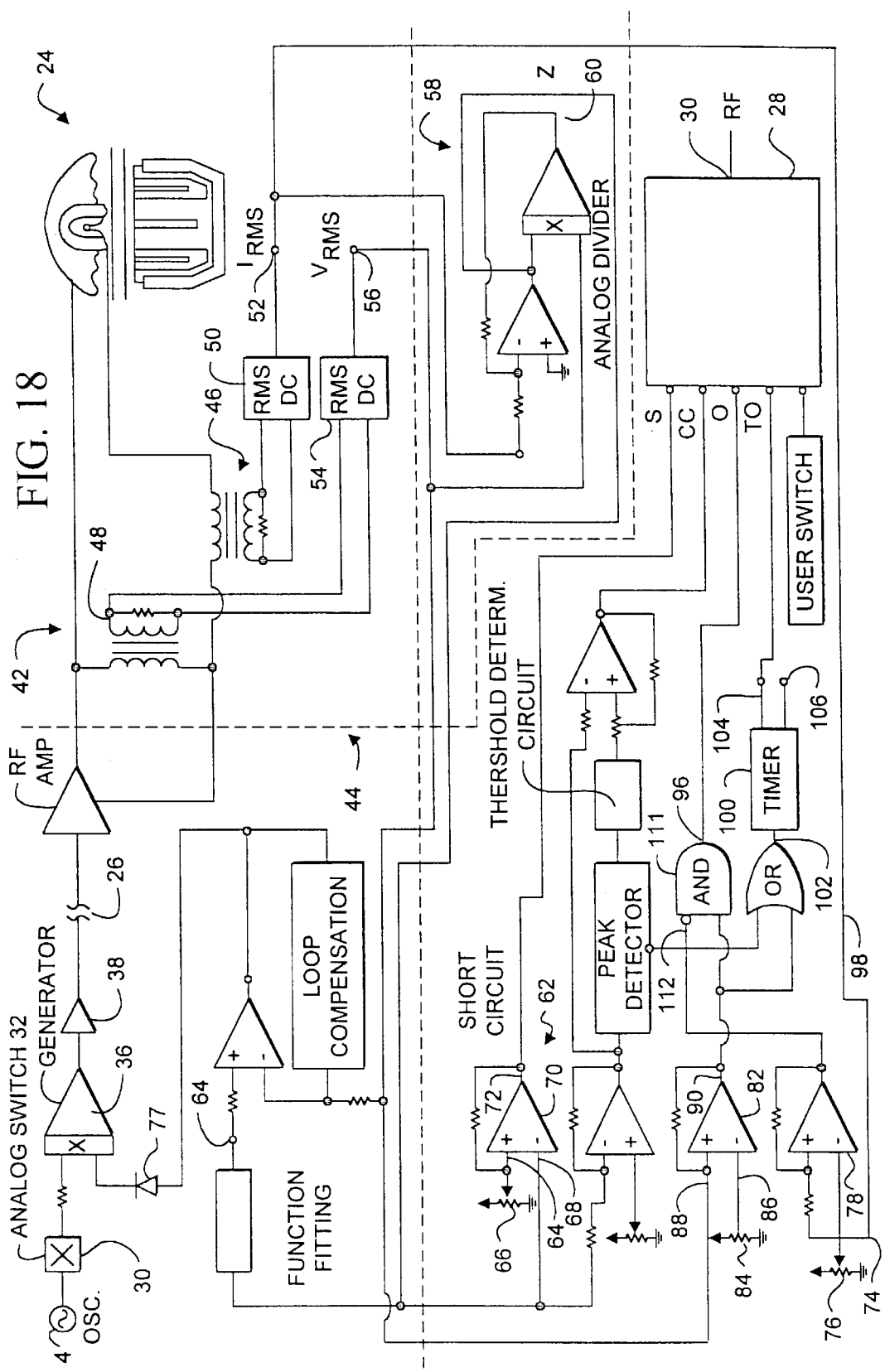
FIG. 18 is a schematic diagram of an analog embodiment of the controller for use in the apparatus of FIG. 1.
Figure 19:
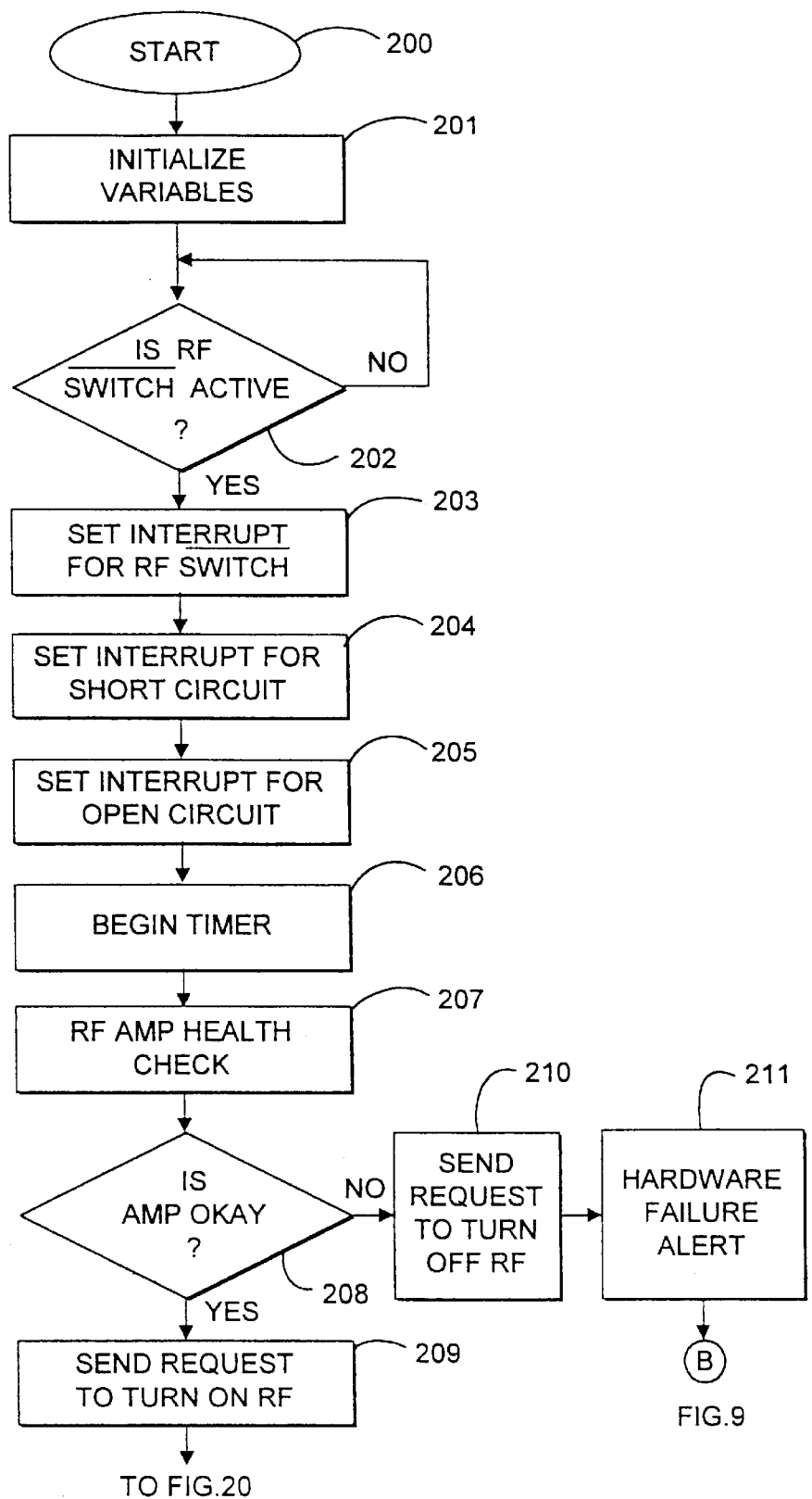
FIGS. 19 through 22 represent a schematic block diagram of a microprocessor controlled impedance monitoring apparatus for controlling RF energy delivered by the apparatus of FIG. 1.
Figure 20:
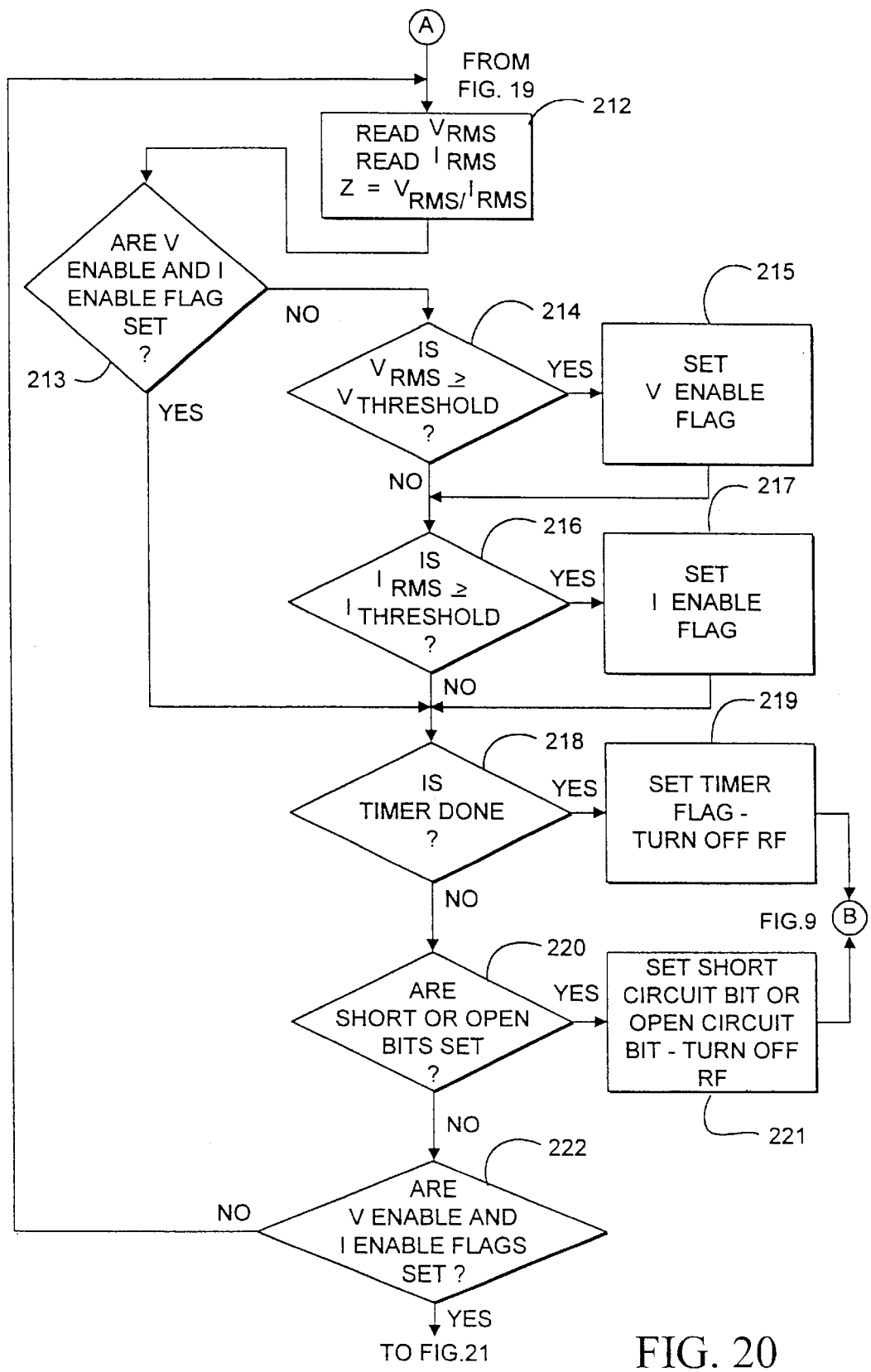
Figure 21:
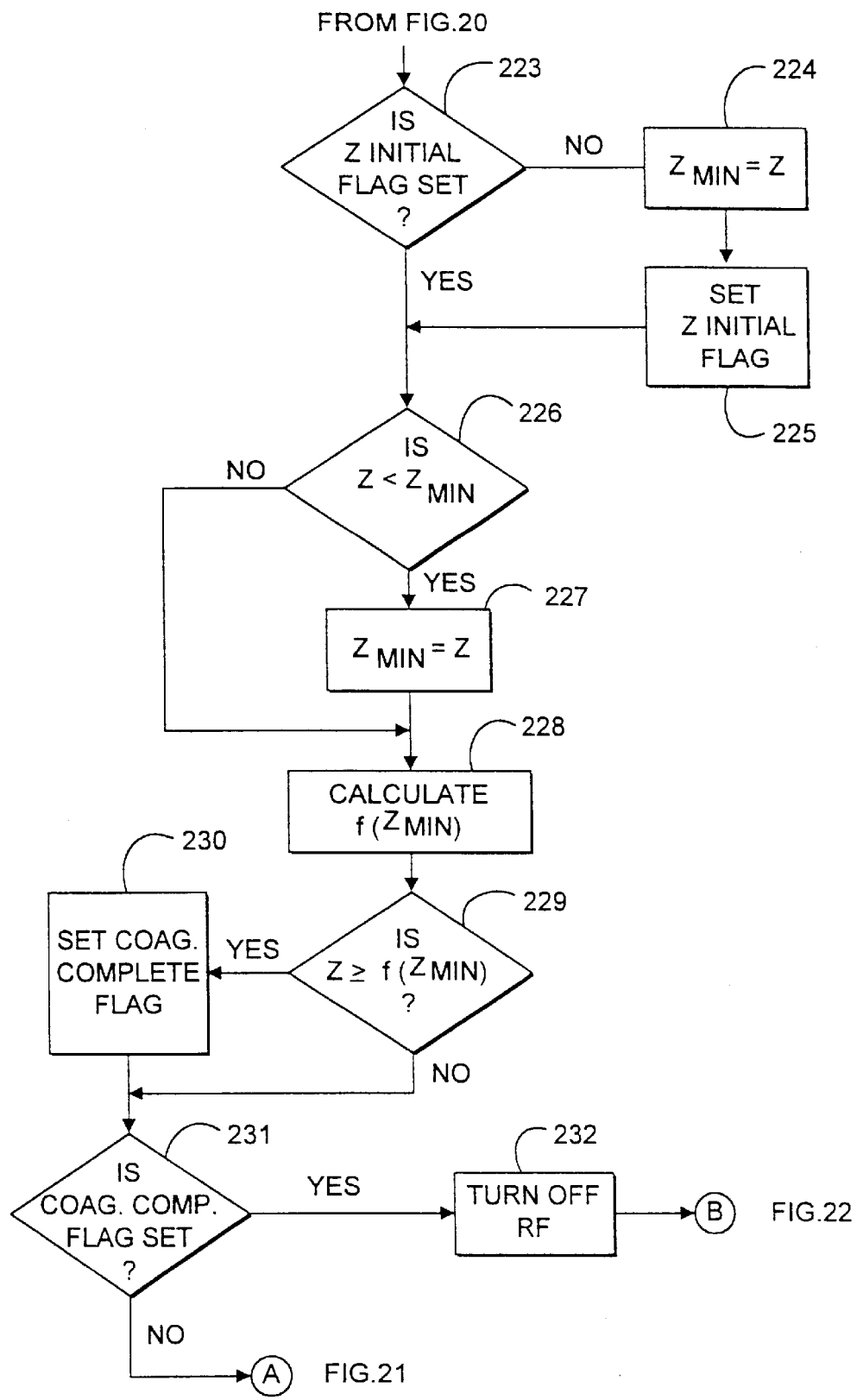
Figure 22:
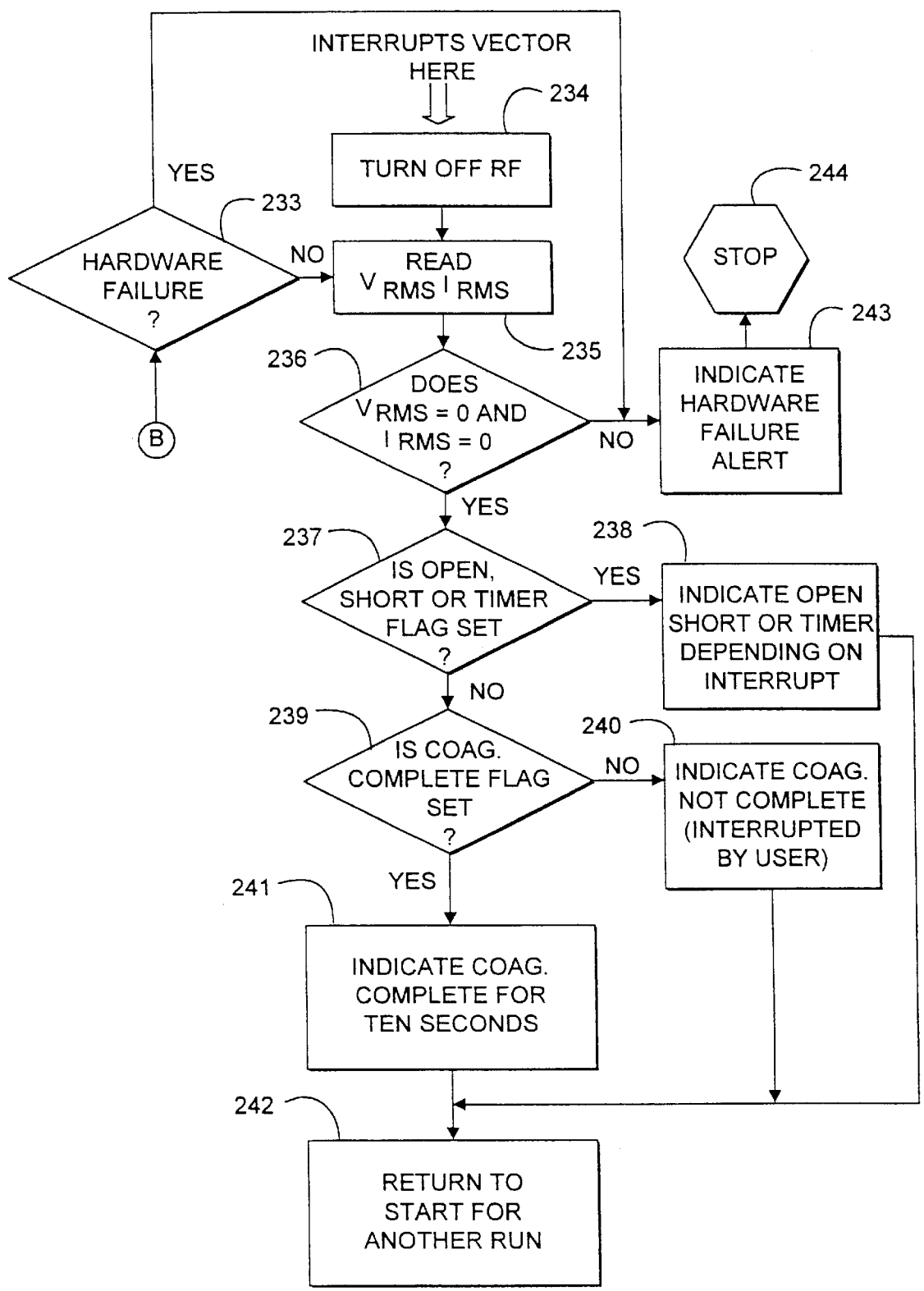

FIG. 18 illustrates a schematic block diagram of an analog embodiment of a specific impedance monitoring device 24 that can be used with apparatus 12 and be incorporated into a feedback control system. Impedance monitoring device 24 is used to control the delivery of electromagnetic and mechanical energy to the skin surface and underlying soft tissue structure to minimize, and even eliminate, cell necrosis as well as blistering of the skin surface. Impedance monitoring device 24 monitors other parameters including but not limited to, if there is an open circuit, short circuit or if voltage and current is supplied to the tissue for more than a predetermined maximum amount of time. Such conditions may indicate a problem with apparatus 12. When energy delivery device 18 is one or more RF electrodes, a generator 26 supplies RF energy to the energy delivery surface 20. Generator 26 is turned on by a user operated switch and provides a signal to controller 28 to turn on the energy. An output 30 of controller 28 is coupled to an analog switch 32. When output 30 provides an "RF on" signal to the switch 32 an oscillator 34 coupled to an analog multiplier 36 through switch 32, supplies a voltage of a known frequency to analog multiplier 36. An output of analog multiplier 36 is coupled to a driver 36 which is coupled to the input of an RF amplifier 40. An amplified RF signal is supplied by generator 26 to a circuit 42. Current and voltage delivered to tissue is measured and an RMS current ("I sub RMS") and an RMS voltage ("V sub RMS") are determined. A voltage and current sensor 44 senses the current and voltage delivered to tissue. Voltage and current sensor 44 includes a low impedance current transformer 46 in series with generator 26 and a high impedance voltage transformer 48 connected in parallel across generator 26. Current transformer 46 may have a 1:20 winding ratio and a 50 ohm resistor in parallel with a secondary of low impedance current transformer 46. Voltage transformer 48 may have a 20:1 winding ratio and a 1K ohm resistor in parallel with the secondary of low impedance current transformer 46.

The output of low impedance current transformer 46 is coupled to an RMS converter 50. RMS converter 50 converts a sensed current to a DC signal to provide output 52, representative of I sub RMS. The output of voltage transformer 48 is coupled to an RMS converter 54. RMS converter 54 converts the voltage signal into an DC signal and provide output 56, representative of V sub RMS.

The measured impedance, Z, is then calculated from the measured I sub RMS and V sub RMS. Outputs 56, 54 of V sub RMS and I sub RMS are supplied to an analog divider 58 which divides the V sub RMS by the current I sub RMS to provide an output signal 60 representative of the measured impedance Z.

From the I sub RMS, V sub RMS and measured impedance Z, impedance monitoring circuit 24 determines whether, (i) a short circuit or open circuit condition exists, (ii) voltage and current has been delivered for an amount of time exceeding a predetermined maximum and (iii) whether controlled remodeling, contraction, tightening, smoothing and the like is complete.

A short circuit condition is determined by comparing measured impedance Z to a predetermined short circuit impedance threshold at or below which short circuit is likely to exist ("Z sub SC"). If the measured Z is at or below the Z sub SC, a short circuit signal is provided to controller 28.

Impedance signal 60 is input to a short circuit detector 62 comprised of a comparator. A positive input 64 of the comparator is connected to a potentiometer 66 which sets the threshold impedance, Z sub SC. When impedance signal 60 causes the input at a negative input 68 of a comparator 70 to be lower than that at positive input 64, an "on" condition occurs at an output 72 of comparator 70. This condition is communicated to a logic controller which provides a preprogrammed response that can include turning off RF energy.

A current threshold detector 74 includes a potentiometer 76 coupled to a negative input 78. Potentiometer 76 sets the I sub thresh level so that when a current is present, current detector 74 will indicate as such. The I sub RMS signal 86 is connected to a positive input 80 of current threshold detector 74. Thus, when the I sub RMS is greater than the value, I sub thresh, set by the potentiometer 76, a positive voltage appears at an output of current threshold detector 74.

Similarly, a voltage threshold detector 82 includes a potentiometer 84 connected to a negative input 86. Potentiometer 84 sets the voltage threshold at which threshold detector 82 registers a positive output, V sub thresh, when a minimum voltage is present. The V sub RMS signal is input to a positive input 88 of the threshold detector 82. If V sub RMS exceeds V sub thresh set by potentiometer 84 a positive voltage appears at an output 90 of voltage threshold detector 82.

Output 90 of the voltage threshold detector 82 is also coupled to an AND gate 92 and the output of current threshold detector 74 is coupled to an inverted input 94 of AND gate 92. AND gate 92 acts as an open circuit detector. When V sub RMS exceeds V sub thresh and where the I sub RMS does not exceed I sub thresh, a logic 1 (not shown) will appear at an output 96 of AND gate 92 indicating an open circuit. Output 96 of AND gate 92 is coupled to controller 28 to communicate the open circuit status.

The output of current threshold detector 74 is coupled to an OR gate 98 which is coupled to a timer 100. If I sub RMS exceeds I sub thresh, the output of current threshold detector 74 will present a logic 1 to the OR gate 98 which will then turn on the timer 100.

Similarly output 90 of voltage threshold detector 82 is coupled to OR gate 98. If V sub thresh is exceeded by V sub RMS, OR gate 98 will present a logic 1 at its output 102 and turn on timer 100. An output 104 of timer 100 is coupled to controller 28. When timer 100 has been activated for an amount of time that exceeds a preset threshold time, T sub max, output 104 will be a logic 1. Timer 100 is reset with a user activated switch that is coupled to the timer reset input 106, when apparatus 10 is reset.

A continuous comparison is made between Z and f(Z sub min). It should be noted here that f(Z sub min) is continuously calculated as f(Z) until a Z sub min is detected. The comparison is continuously made between Z and f(Z) until Z sub min is determined.

If measured Z is less than or equal to the Z sub target then RF energy is continued to be supplied and steps described above are carried out until a signal has been provided to controller 28 that there is an open circuit signal, short circuit signal or a time over signal. If the measured Z is greater than or is equal to "Z sub target" then a signal is provided to controller 28. It is noted that in this embodiment, Z has been inverted and shifted in order to accommodate Z sub min determination.

A control device which controls an RF generator energy output based on load impedance. The load impedance is used to determine a preferred energy level, e.g., voltage, current or power level, based on a specific system load curve for generator 26, other power sources and/or application. The control device then compares the actual energy level for measured impedance with the desired energy level and adjusts the generator output according to the difference between the two, i.e., preferably to minimize the difference between the two.

The specific load curve preferably reflects the voltage, current, power, for a range of impedance that will optimize performance of apparatus 10 for a variety of different procedures and anatomical body structures. The load curve may have various forms, for example, it may be continuous or may be stepped. The load curve may vary from power source to power source, or for different body structures and/or applications. In a one embodiment using apparatus 10, different impedance ranges may be identified at which different energy requirements exist. Initially tissue impedance is in a lower range. In the lower ranges more current is required to provide enough power. A second, mid-range of impedances requires enough power to maintain the process. A third range of higher impedances may be required at the end of the process.

Referring now to FIGS. 19 through 22 a flow chart illustrates a method for carrying out a microprocessor controlled embodiment of the present invention. When the system is turned on (block 200), the variables including Z sub min, V sub thresh, I sub thresh, time over, and Z sub initial, are initialized (block 201). The system continues to look for the activation of the RF switch (block 202). When the RF switch is turned on, the interrupts are set for RF Switch (block 203), for Short Circuit (block 204), and Open Circuit (block 205) so that when one of these interrupt conditions occur, the microprocessor automatically goes to the instructions associated with block 234.

After the interrupts are set, the timer is started (block 206). A sequence is run to check the RF amplifier health (block 207), e.g., to look for an Amplifier On signal or to check if certain voltages are in a suitable range. If the amplifier is operating properly, RF energy is turned on (blocks 208 and 209).

If the amplifier is not operating correctly, an RF Off request is made (blocks 209 and 210) and a Hardware Failure Alert flag is set (block 211). The system looks for a hardware failure flag (block 233). When the hardware failure is detected, the controller provides a hardware failure alert indication and shuts off. (blocks 243 and 244).

If hardware failure is not indicated (block 233), then V sub rms and I sub rms is read (block 235) to determine if any voltage or current is being supplied by the system (block 236). When the system is first initialized, until the instruction to turn on energy in block 209 is reached, there should be no current or voltage. If there is a voltage or current with the RF request off, then there is a hardware failure. A hardware failure alert is indicated and the program is stopped (blocks 243 and 244).

If RF energy is turned on (block 209), then the V sub rms and I sub rms are read and the impedance, Z, is calculated by dividing the V sub rms by the I sub rms. (block 212). The controller checks to see if the V sub enable and I sub enable flags are set. (block 213). These flags are set when a minimum threshold voltage is present and a minimum threshold current is delivered through the electrodes of the device. (blocks 214, 215, 216, and 217).

If the V sub enable and I sub enable flags are set (213) the software looks for a time over condition to determine if the device has been on for a period of time in excess of a maximum. If a time over condition is recognized, the timer flag is set, RF energy is turned off (blocks 218 and 219) and a hardware failure check is run (block 233).

After looking for a time over condition, the controller checks for a short circuit or open circuit condition. If a short or open circuit exists, the corresponding short circuit or open circuit bit is set (block 220), RF energy is turned off (block 221), and a hardware failure check is run (block 233).

The controller checks again for V sub enable and I sub enable in block 222, before proceeding to the threshold determining portion of the circuit illustrated in FIG. 8. If the voltage or current did not exceed V sub thresh or I sub thresh in blocks 214 and 216, the controller iterates the sequence beginning at block 212 for detecting time over, short circuit, open circuit, i.e., the coagulation complete detection enable. This enables the device to wait until enough current and voltage is delivered to the circuit to check for the coagulation complete condition.

If the V sub enable and I sub enable flags are set, the short circuit and open circuit bits are not set (block 220), and the time over condition does not yet exist (block 219), the measured impedance used to determine if coagulation is complete as follows.

The Z initial flag is set during the first iteration and Z sub min is initially assigned the measured impedance value (blocks 223–225). Initially, Z sub min is the same as the measured impedance and thus block 227 is bypassed at block 226. A calculation is made of f(Z sub min) (block 228). As long as the measured impedance is less than the f(Z sub min), the sequence is iterated (229, 231). In the next iteration of blocks 223–231, the newly measured impedance is compared to the previous measured impedance which has been assigned Z sub min (block 226). As long as the impedance is decreasing, Z sub min will be reassigned the new value of the measured impedance (blocks 226 and 227) and the steps repeated. When the measured impedance is greater than or equal to f(Z sub min), i.e. the threshold impedance, the coagulation complete flag is set (block 230). If coagulation complete flag is set, the RF is turned off (block 232) and the hardware failure check is run.

If after the initial run through the program a hardware failure alert occurs (block 233, 236) or an interrupt occurs, the program determines the cause and indicates as such (blocks 233–242). The V sub rms and I sub rms are read, (block 235). If no current or voltage is being delivered to the system, the controller checks to see if the open circuit, short circuit or time over flags have been set (block 237). If so then a signal indicates which flags have been set, and the program is returned to start (blocks 240, 242). Similarly, the controller checks for the coagulation complete flag (block 239). If there was the coagulation complete flag has been set, it will be indicated for ten seconds (block 241). If not, it will be indicated as not complete (block 240) and the program will return to point at the start (block 242). Preferably the electrical components selected to carry out the steps of FIGS. 17 through 20 are adapted to provide a complete iteration of all the steps at least every $\frac{1}{50}$ second.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A method for smoothing contour irregularities of a skin surface overlaying a tissue site, comprising:
   applying to the skin surface a conformer which is dimensionally conformable, includes a mechanical force application surface, and is coupled with an electromagnetic energy delivery device;
   applying positive mechanical force through the mechanical force application surface to the tissue site, such that the conformer conforms to the general three-dimensional contour of the tissue site;
   producing electromagnetic energy from the electromagnetic energy delivery device;
   compressing the conformer by an external mechanical force to produce converging and diverging vectors that smooth skin surface morphology by contracting and distracting the collagen matrix in the soft tissue structure beneath the skin surface;
   delivering electromagnetic energy produced by the electromagnetic energy delivery device through the skin surface to the tissue site while the conformer is being compressed; and
   applying a sufficient amount of electromagnetic energy to the tissue site through the skin surface to remodel at least a portion of the tissue site and smooth contour irregularities of the skin surface.

2. The method of claim 1, further comprising:
   providing a chemical means with an agent to induce an inflammatory reaction of the skin surface; and
   inducing an inflammatory wound healing sequence with the chemical means.

3. The method of claim 1, further comprising:
   providing a chemical means with an agent to induce an inflammatory reaction of the skin; and
   inducing an inflammation and smoothing of the skin surface.

4. The method of claim 1, wherein the electromagnetic energy delivered to the tissue site does not exceed 1000 joules/cm2 during a single treatment session.

5. The method of claim 1, wherein the electromagnetic energy delivered to the tissue site underlying the skin surface does not exceed 600 joules/cm2 during a single delivery of energy.

6. The method of claim 1, further comprising:
   hydrating the skin surface.

7. The method of claim 1, further comprising:
   cooling the skin surface.

8. The method of claim 1, further comprising:
   controlling a dose rate of electromagnetic energy to the skin surface not exceeding 10 joules/sec/cm2.

9. The method of claim 1, further comprising;
   controlling a dose rate of electromagnetic energy to the skin surface not exceeding 200 joules/sec/cm2.

10. The method of claim 1, further comprising;
    controlling the delivery of electromagnetic energy to the skin surface to operate in an impedance range of 70 ohms cm2 measured at a frequency of 88 Hz to 40 Kohms cm2 measured at a frequency of 10 KHz.

11. The method of claim 1, further comprising:
    controlling the delivery of electromagnetic energy to operate in a range of thermal conductivity at a surface of the structure of 0.21 to 0.60 k.

12. The method of claim 1, further comprising:
    controlling a delivery of electromagnetic energy to operate in a range of compression force applied to the skin surface not exceeding 300 mmHg.

13. The method of claim 1, further comprising:
    controlling a delivery of electromagnetic energy to operate in a range of compression force applied to the skin surface not exceeding 200 mmHg.

14. The method of claim 1, further comprising:
    controlling a delivery of electromagnetic energy to operate in a range of compression force applied to the skin surface not exceeding 100 mmHg.

15. The method of claim 1, further comprising:
    detecting a temperature of the skin surface.

16. The method of claim 15, wherein applying a sufficient amount of electromagnetic energy to the tissue site includes applying a sufficient amount of electromagnetic energy to the tissue site in response to the detected temperature of the skin surface to remodel at least a portion of the tissue site and smooth contour irregularities of the skin surface.

17. The method of claim 1, further comprising:
    creating a reverse thermal gradient through the skin surface, wherein a temperature of the skin surface is less than a temperature of the tissue.

18. The method of claim 1, wherein the contour irregularities of the skin surface include wrinkles, loose skin and cellulites.

* * * * *